United States Patent
Murphy et al.

(10) Patent No.: US 11,098,361 B2
(45) Date of Patent: Aug. 24, 2021

(54) USE OF SHROOM3 IN CHRONIC KIDNEY DISEASE AND CHRONIC ALLOGRAFT NEPHROPATHY

(71) Applicant: ICAHN SCHOOL OF MEDICINE AT MOUNT SINAI, New York, NY (US)

(72) Inventors: Barbara Murphy, Pelham Manor, NY (US); John Cijiang He, Forest Hills, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 14/773,687

(22) PCT Filed: Mar. 10, 2014

(86) PCT No.: PCT/US2014/022607
§ 371 (c)(1),
(2) Date: Sep. 8, 2015

(87) PCT Pub. No.: WO2014/159227
PCT Pub. Date: Oct. 2, 2014

(65) Prior Publication Data
US 2016/0032384 A1    Feb. 4, 2016

Related U.S. Application Data

(60) Provisional application No. 61/777,328, filed on Mar. 12, 2013.

(51) Int. Cl.
*C12Q 1/6883* (2018.01)

(52) U.S. Cl.
CPC ...... *C12Q 1/6883* (2013.01); *C12Q 2600/118* (2013.01); *C12Q 2600/136* (2013.01); *C12Q 2600/156* (2013.01); *C12Q 2600/158* (2013.01); *G01N 2500/10* (2013.01); *G01N 2800/245* (2013.01); *G01N 2800/347* (2013.01); *G01N 2800/50* (2013.01)

(58) Field of Classification Search
None
See application file for complete search history.

(56) References Cited

U.S. PATENT DOCUMENTS

2010/0022627 A1    1/2010   Scherer

FOREIGN PATENT DOCUMENTS

| JP | 2009-532047 | 9/2009 |
|----|-------------|--------|
| WO | WO 2007/112999 | 10/2007 |
| WO | WO 2009/097593 | 8/2009 |
| WO | WO 2013/013708 | 1/2013 |
| WO | WO 2007/029249 | 1/2015 |

OTHER PUBLICATIONS

Nature Genetics. 2010. 42(5): 376-384 and "Online Methods", 2 pages.*
Menon et al American J of Transplantation. May 2012. 12(3): 184, abstract #520.*
Shriner et al. PLoS ONE. 2012. 7(9): e45112.*
Hirschhorn et al. Genetics in Medicine. vol. 4, No. 2, pp. 45-61, Mar. 2002.*
Lucentini et al The Scientist (2004) vol. 18, p. 20.*
Hattersley et al. The Lancet. 2005. 366: 1315-1323.*
NCBI dbSNP. Submission ss24326022 for rs17319721. (Aug. 21, 2004. National Center for Biotechnology Information. National Library of Medicine. Bethesda, MD, USA.*
Boger et al., "Association of eGFR-Related Loci Identified by GWAS with Incident CKD and ESRD," *PLOS Genetics.*, 7(9):e1002292, 8 pages, Sep. 29, 2011.
Ellis et al., "Validated SNPs for eGFR and their associations with albuminuria," *Human Molecular Genetics.*, 21(14):3293-3298, Apr. 5, 2012.
Extended European Search Report in Application No. 14773719.1, dated Feb. 3, 2017, 16 pages.
Hauser I.A., "ABCB1 Genotype of the Donor but not of the recipient is a major risk factor for cyclosporine-related nephrotoxicity after renal transplantation," *J Am Soc Nephrology.*, 16(5):1501-1511, Mar. 30, 2005.
Kottgen et al., "Multiple new loci associated with kidney function and chronic kidney disease: the CKDGen consortium," *Nat Genet.*, 42(5):376-384, May 2010.
Menon et al., "Intronic locus determines SHROOM3 expression and potentiates renal allograft fibrosis," *J Clin Inves.*, 125(1):208-221, Jan. 2015.
Menon et al., "SHROOM3 Is a Predictor of Fibrosis in CAN and CKD," *Am J Transplant.*, 13(suppl 5):Abstract 210, May 2013, Accessed Apr. 19, 2017, Retrieved from the Internet: URL http://www.atcmeetingabstracts.com/abstract/shroom3-is-a-predictor-of-fibrosis-in-can-and-ckd/, 5 pages.
Okada et al., "Meta-analysis identifies multiple loci associated with kidney function-related traits in East Asian populations," *Nature Genetics.*, 44(8):904-909, Jul. 15, 2012.
Partial Supplementary European Search Report in Application No. 14773719.1, dated Oct. 28, 2016, 10 pages.
International Search Report for PCT/US2014/022607 dated Jun. 2, 2015. 2 pages.
Kottgen et al., "New loci associated with kidney function and chronic kidney disease", Nat Genet. 42(5): Apr. 11, 2010; pp. 376-384.

(Continued)

*Primary Examiner* — Carla J Myers
(74) *Attorney, Agent, or Firm* — Fish & Richardson P.C.

(57) ABSTRACT

A method for identifying the risk of developing Chronic Allograft Nephropathy (CAN) in a patient that received a kidney transplant from a donor which comprises identifying the race of the donor; determining the levels of SHROOM 3 expression in a kidney biopsy specimen obtained from the patient at a predetermined time after transplant; comparing the level of SHROOM 3 expression in the biopsy specimen with the levels of SHROOM 3 expression in a control; determining if the level of SHROOM 3 expression in the allograft is significantly higher than in the control, and diagnosing the patient as being at risk for CAN if the level of SHROOM 3 expression in the specimen is significantly higher than in the control.

9 Claims, 22 Drawing Sheets
Specification includes a Sequence Listing.

(56) References Cited

OTHER PUBLICATIONS

Kottgen et al., "Multiple loci associated with indices of renal function and chronic kidney disease", Nat Genet, 41(6), May 10, 2009, pp. 712-717.
Lin et al., "Angiotensin converting enzyme inhibition in chronic allograft mephropathy", Transplantation, Mar. 15, 2002, pp. 783-785.
Aarhus et al., "Microarray-based gene expression profiling and DNA copy number variation analysis of temporal fossa arachnoid cysts", Cerebrospinal Fluid Research, 2010, 8 pages.
Karlsson et al., "Gene expression profiling demonstrates that TGF-beta1 signals exclusively through receptor complexes involving Alk5 and identifies targets of TGF-beta signaling," Physiol Genomics, 2005, 21: 396-403.
Nakamura, "Mineral and bone disorder in kidney transplant recipients," Angiology Frontier, Dec. 2012, 11: 318-326.
Office Action in Australian Application No. 2014241058, dated Jan. 5, 2018, 7 pages.
Office Action in Chinese Application No. 201480026706.3, dated Jul. 23, 2018, 10 pages (with English translation).
Office Action in European Application No. 14773719.1, dated May 24, 2018, 4 pages.
Office Action in Israeli Application No. 241284, dated Jul. 19, 2018, 5 pages (with English translation).
Office Action in Japanese Application No. JP 2016-501011, dated Mar. 1, 2018, 18 pages (with English translation).
Sevilla-Perez et al., "Shroom expression is attenuated in pulmonary arterial hypertension," Eur Respir J, 2008, 32: 871-880.
EP Extended European Search Report in European Appln. No. 20204402.0, dated Apr. 19, 2021, 11 pages.

\* cited by examiner

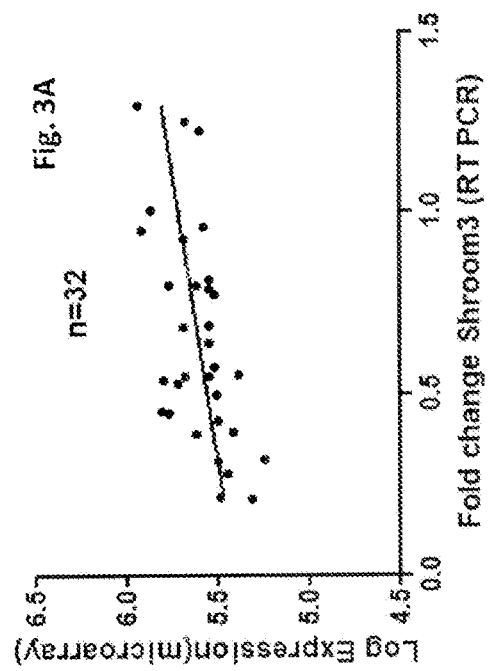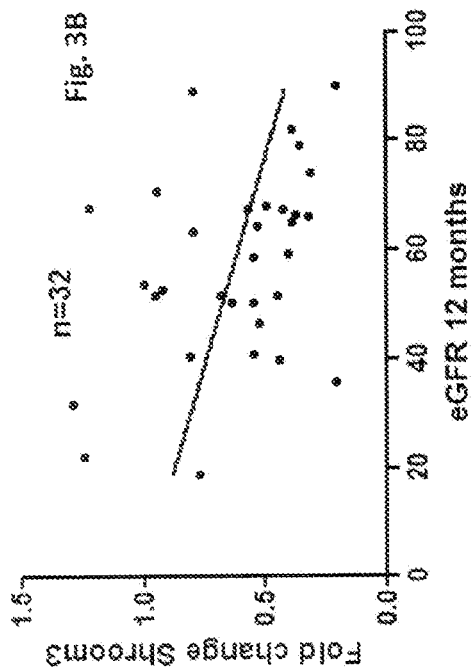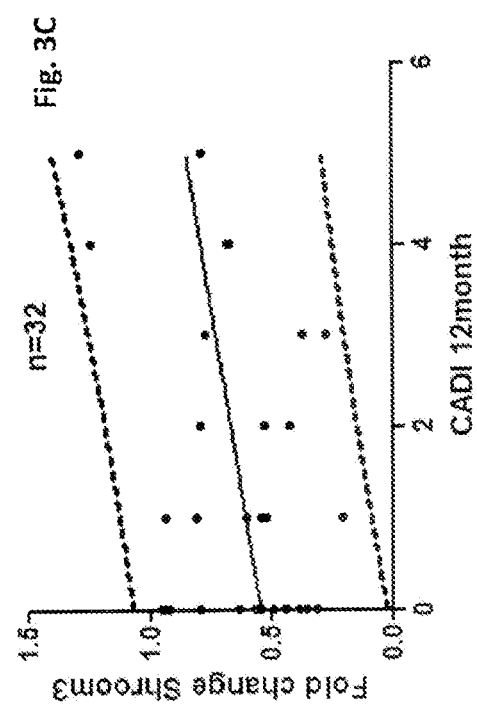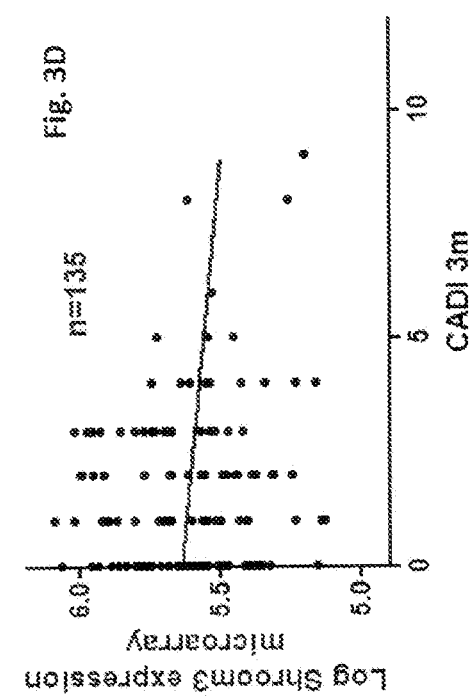
Fig. 3A
Fig. 3B
Fig. 3C
Fig. 3D

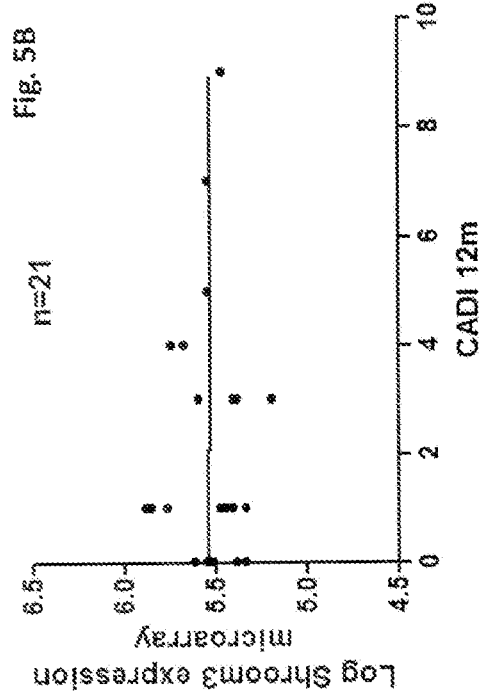
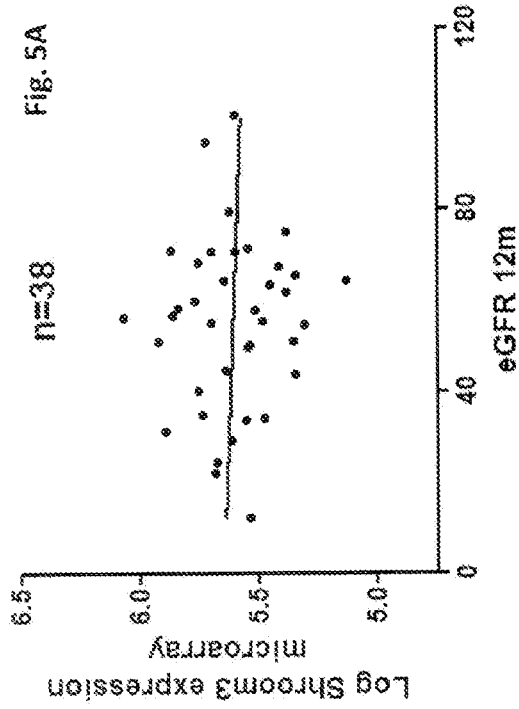
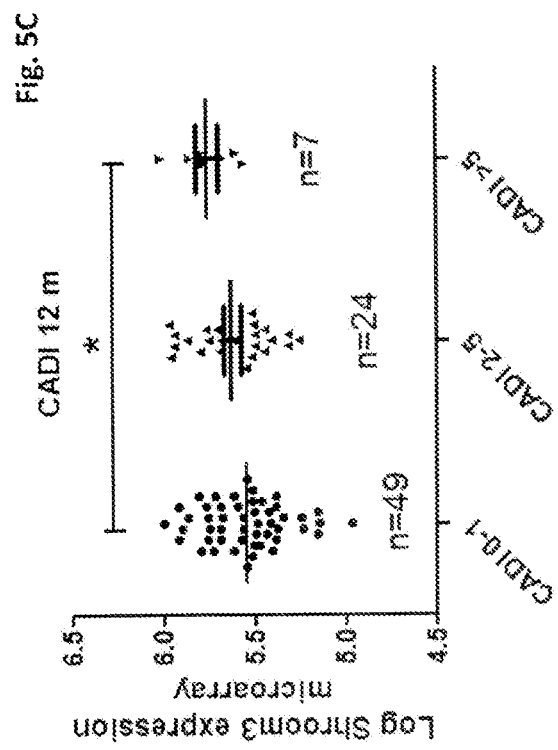

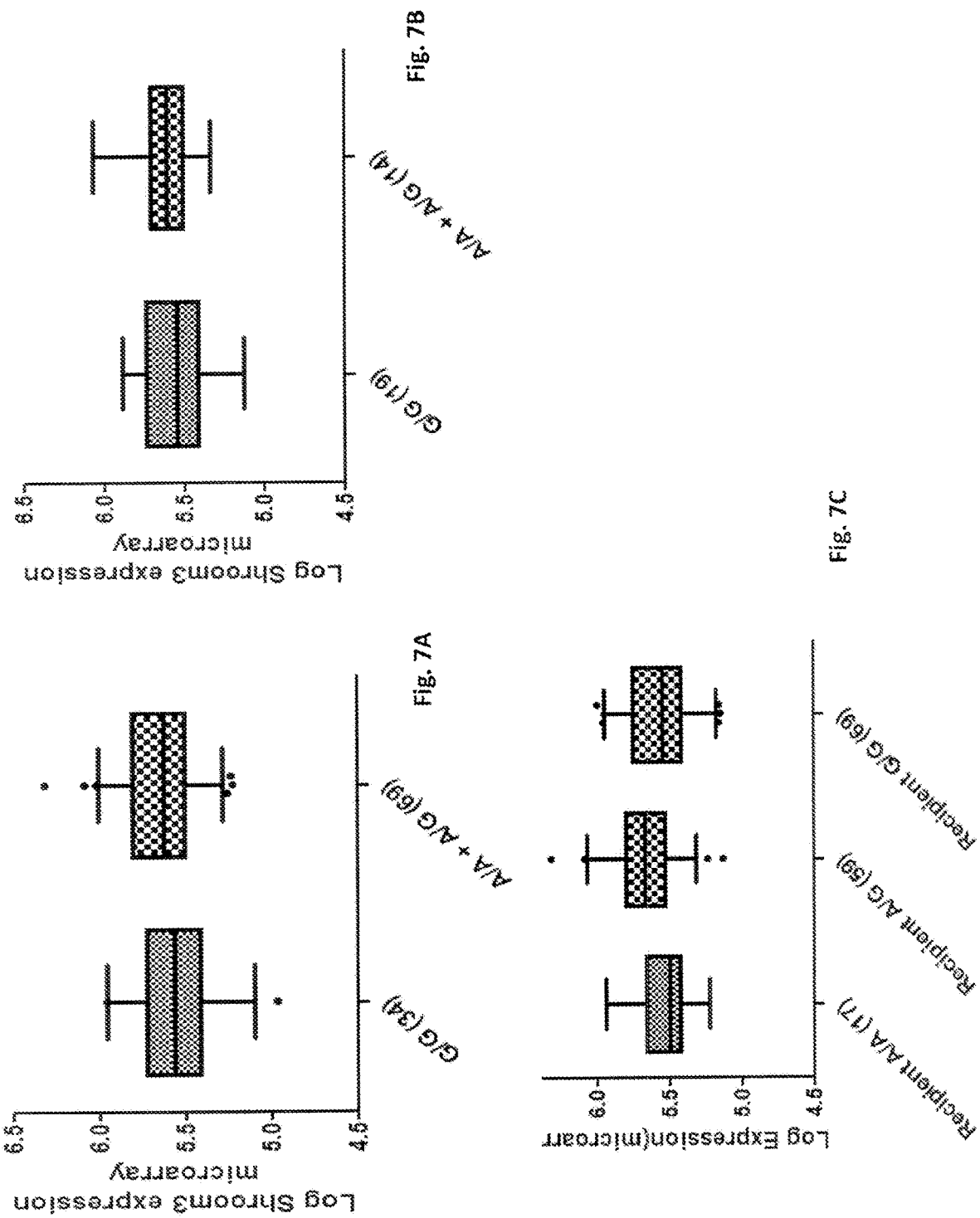

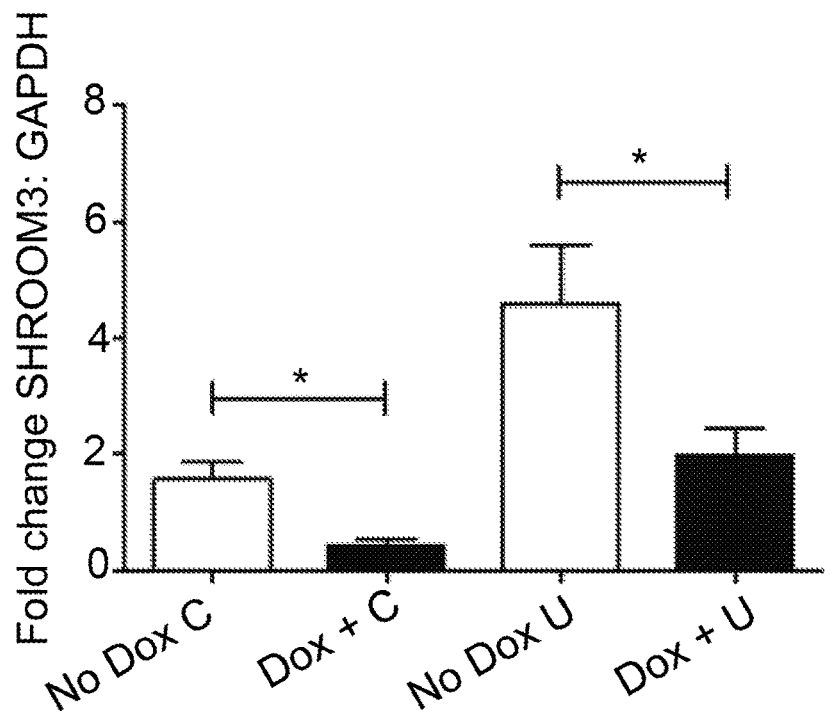
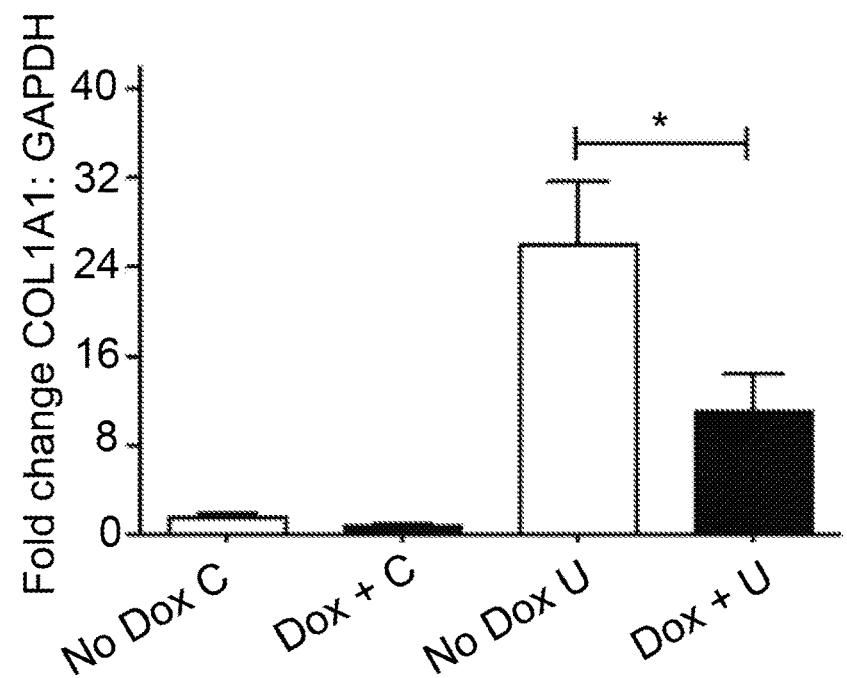
FIG. 16D

USE OF SHROOM3 IN CHRONIC KIDNEY DISEASE AND CHRONIC ALLOGRAFT NEPHROPATHY

CROSS-REFERENCE TO RELATED APPLICATIONS

This is the U.S. National Phase Application under 35 U.S.C. § 371 of International Patent Application No. PCT/US2014/022607 filed Mar. 10, 2014, which claims the benefit of U.S. Provisional Application No. 61/777,328 filed Mar. 21, 2013, both of which are incorporated by reference herein. The International Application was published in English on Oct. 2, 2014 as WO2014/159227 A1 under PCT Article 21(3).

GOVERNMENT CLAUSE

This invention was made with government support under 1U01A1070107-01 awarded by The National Institutes of Health. The government has certain rights in the invention.

FIELD OF THE INVENTION

The present invention pertains to methods to identify patients suffering from kidney diseases and predict the development and progression of kidney fibrosis in renal allograft recipients. The invention includes a kit for identifying patients suffering from kidney diseases and for predicting the development and progression of kidney diseases and tubulo-interstitial fibrosis in renal allograft recipients.

BACKGROUND OF THE INVENTION

Chronic Kidney disease (CKD) affects 10% of US adults with rising incidence and prevalence worldwide {Coresh J, 2007}. End-stage renal disease (ESRD) requires renal replacement therapy (RRT) and currently affects over 500,000 US adults. In addition to conferring risk for end stage renal disease (ESRD), CKD increases the risk of cardiovascular disease and all-cause mortality {Weiner D, 2004}. Tubulo-interstitial fibrosis (TIF) is a final common pathogenic process for CKD from varied etiologies leading to the development of ESRD. TIF is also a primary component of chronic allograft nephropathy (CAN) and is associated with progressive decline of estimated glomerular filtration rate (eGFR) in the renal allograft {Chapman J, 2005} {Nankivell B J, 2003}. CAN represents the most common cause of death-censored long-term graft loss and is measured histologically by the chronic allograft dysfunction index score (CADI score) {Isoniemi H, 1992} {Yilmaz S, 2007}. To date, there is no effective anti-fibrotic therapy to prevent the progression of CKD or CAN. Presently, some patients with CKD or CAN will eventually progress to ESRD and need RRT. For instance, renal allograft recipients represented 13.5% of patients on the kidney transplant waitlist and 15% of all transplants performed in 2005 {Magee J C, 2007}. Renal allograft recipients have a 30% probability of requiring RRT or re-transplantation at 10-years {USRDS 2012}. RRT and ESRD-care are a disproportionate and burgeoning financial burden to Medicare {Iglehart, 2011}. It is therefore critical to identify new sensitive biomarkers to predict the development of kidney fibrosis. Furthermore, these markers could represent targets for therapeutic intervention to prevent the development of TIF at an early stage, thereby preventing progression to ESRD.

Allograft biopsy based studies (both for-cause and protocol) have provided insight into how early allograft changes correlate with long term allograft outcomes {Gago M, 2012} {Rush D, 1994} {Seron D, 1997} {Cosio F, 2005} {Park W, 2010}. More recently, distinct biopsy and blood gene-expression profile (transcriptome) signatures have been shown to classify patients with acute rejection, chronic rejection, those on immunosuppression, and operationally tolerant recipients {Akalin E, 2010} {Akalin E, 2001} {Flechner S, 2004} {Donauer J, 2003} {Sarwal M, 2003} {Reeve J, 2009} {Scherer A, 2003} {Sagoo P, 2010} {Newell K, 2010}. These gene panels have been able to improve upon histological classifiers alone {Sarwal M, 2003} {Reeve J, 2009}. Genome-wide association studies have also strongly linked a single-nucleotide polymorphism (SNP) in the Shroom3 gene (rs17319721) with incident and prevalent CKD by eGFR in population-based cohorts of European ancestry {Kottgen A, 2009} {Boger C, 2011}. The Shroom3 gene encodes a PDZ domain-containing protein that can directly bind F-actin and regulate its subcellular distribution in cells. Complete absence of or defective Shroom3 causes open neural tube defects and neonatal death in mice {Hildebrand J, 1999}. In MDCK kidney cell lines, Shroom3 localizes at the apical and junctional complexes and is critical to the maintenance of normal epithelial cell phenotype {Hildebrand J, 2005}. It is also known that C-terminal domain of Shroom3 interacts with Rho-Kinases (ROCKs) to facilitate myosin phosphorylation and actin contraction {Nishimura T, 2008}. However, whether Shroom3 plays a role in kidney fibrosis in CKD or CAN is yet unknown.

What are needed in the art are markers whose expression can be used to identify patients suffering from kidney diseases and predict the development of kidney fibrosis. In addition, such markers are needed to identify renal allograft recipients who are at risk for developing CAN and represent targets for therapeutic intervention to prevent the development of TIF at an early stage, thereby preventing progression to ESRD.

SUMMARY OF THE INVENTION

Shroom3 is a novel candidate gene whose expression in a renal allograft precedes and predicts decreased renal function and TIF. Higher allograft Shroom3 levels predict histological progression of CAN. It has also been found that these relationships correlate best in recipients of white-donor kidneys. The findings confirm for the first time that the previously described chronic kidney disease (CKD)-associated Shroom3 locus (rs17319721) {Kottgen A, 2009} {Boger C, 2011} mediates its effect through increased Shroom3 expression. In addition, it has been discovered that Shroom3 has a salutary role in canonical TGF-beta signaling and Collagen-1 production.

In one aspect, the present invention provides method for identifying the risk of developing Chronic Allograft Nephropathy (CAN) in a patient that received a kidney transplant from a donor which comprises identifying the race of the kidney donor; determining the levels of SHROOM 3 expression in a kidney biopsy specimen obtained from the patient at a predetermined time after transplant; comparing the level of SHROOM 3 expression in the biopsy specimen with the levels of SHROOM expression in a control; determining if the level of SHROOM 3 expression in the allograft is significantly higher than in the control, and diagnosing the patient as being at risk for CAN if the level of SHROOM 3 expression in the specimen is significantly higher than in the control.

In a further aspect the present invention provides a method for identifying the risk of developing Chronic Allograft Nephropathy (CAN) in a patient that received a kidney from a donor comprising the steps of identifying the race of the kidney donor; obtaining a renal allograft biopsy sample from the patient; determining the levels of SHROOM3 expression in said biopsy; comparing the levels of SHROOM3 expression in said biopsy with the levels of SHROOM3 expression in a control and advising the patient as being at risk of developing CAN if the levels of SHROOM3 in the sample are significantly higher than in the control and the kidney donor is Caucasian.

In yet a further aspect, the present invention provides a method for identifying the risk of developing a renal disease in a Caucasian patient that received a kidney from a donor, comprising the steps of determining if said donor expresses the rs 17319721 SNP risk allele and conducting a genetic analysis to determine if said donor is homozygous for said risk allele, wherein if said donor is homozygous for said risk allele then said patient is at risk for developing a renal disease.

In yet a still further aspect, the present invention provides a method for identifying the risk of developing fibrosis in a Caucasian kidney donor, comprising the steps of determining if said donor expresses the rs 17319721 SNP risk allele, and conducting a genetic analysis to determine if said donor is homozygous for said risk allele; wherein if said donor is homozygous for said risk allele then said donor is at risk for fibrosis.

In a still further aspect the present invention provides a method for identifying the risk of developing a progressive kidney disease selected from the group consisting of Chronic Allograft Nephropathy (CAN) and Chronic Kidney Disease (CKD) of a Caucasian patient which comprises: determining the levels of SHROOM 3 expression in a kidney biopsy specimen obtained from the patient at a predetermined time, comparing the level of SHROOM 3 expression in the biopsy specimen with the levels of SHROOM 3 expression in a control, determining if the level of SHROOM 3 expression in the specimen is significantly higher than in the control, and diagnosing the patient as being at risk for said disease if the level of SHROOM 3 expression in the specimen is significantly higher than in the control.

In a still further aspect, the present invention provides a kit for identifying patients suffering from a renal disease and at risk for developing CAN or CKD comprising in separate containers primers for use in RT-PCR assays for SHROOM3 expression, RT-PCR for detecting the rs 17319721 SNP risk allele, a positive control, buffers and instructions for use.

These and other aspects of the present invention will be apparent to those of ordinary skill in the art in light of the present description, claims and drawings.

BRIEF DESCRIPTION OF THE DRAWINGS

FIG. 3A-3D: graphs depicting (3A) the correlation of Fold change Shroom3 expression (RT-PCR) at 3 months and CADI-12 months (Pearson $r=0.4169$; $p=0.0103$); (3B) the correlation of Fold change Shroom3 expression (RT-PCR) at 3 months and eGFR creatinine at 12 months ($r=0.3230$; $p=$(3C) the correlation between allograft log Shroom3 expression (microarray) at 3 months and Fold change Shroom3 expression at 3 months (RT PCR) (Pearson $r=0.5613$; $p=0.0008$); and (3D) the regression line of relationship between log Shroom3 expression at 3 months and simultaneous CADI score—No relationship could be identified FIG. 4A-4C: graphs depicting (4A) the correlation of allograft log Shroom3 expression at 3 months and CADI-12 months in recipients of white-donor kidneys ($r=0.2538$; $p=0.02$); (4B) the correlation of allograft log Shroom3 expression to eGFR-creatinine in recipients of white-donor kidneys ($r=-0.25$; $p=0.008$); and (4C) Log Shroom3 expression was higher in WDKRs with progression of fibrosis (Delta CADI≥2; n=14) vs than those without significant progression (Delta CADI<2; n=56) [*$p<0.05$; $p<0.001$; *$p<0.0001$]

FIG. 5A-5C: graphs depicting that (5A) there is no correlation between allograft log Shroom3 expression (microarray) at 3 months and 12-month CADI in living donor recipients (LDRs) and: (5B) in non-WDKRs; (5C) No correlation between 3-month Shroom3 and eGFR-12m in non-WDKRs.

FIG. 7A-7C: graphs depicting that (7A, 7B, respectively) Shroom3 expression was increased in both WDKRs and non-WDKRs with the presence of effect-allele (A) in the donor and (7C). Shroom3 expression was not significantly affected Recipient SNP type (whiskers: Min-Max; Line at Median; $p=0.0309$) [*$p<0.05$; $p<0.001$; *$p<0.0001$]

FIG. 10A is a graph that depicts that Luciferase-reporter plasmids with A-allele enhancer element showed greater activity than G-allele and promoter-only plasmids; FIG. 10B is a Western Blot that illustrates that Nucleoprotein extracted from 293-T cells showed enhanced binding to oligonucleotide sequences containing the G-allele.

FIG. 11A is a graph illustrating that in PRCEC, TGF-β treatment increases Shroom3 in a dose-dependent (up to 5 ng/ml) and time dependent fashion by RT-PCR (error bars: mean in PRCEC, TGF-β treatment increases Shroom3 in a time dependent fashion (up to 5 ng/ml) (error bars: mean±SEM) [*p<0.05; p<0.001; *p<0.0001]. FIG. 11B is a Western Blot that illustrates that TGF-β treatment increases Shroom3 in a time-dependent fashion.

FIG. 12A is a graph that depicts the results of Example 6 that shows TGF-beta increases Shroom3 expression in a beta-Catenin/TCF712 dependent manner. Quercetin (beta-Catenin inhibitor) and BC-21(TCF7L2 inhibitor) inhibited the increase in Shroom3 expression induced by TGF-beta (RT-PCR). 12B is a Western blot that depicts Shroom3 protein increases in a Beta-Catenin/TGF-β dependent manner.

FIG. 13A is a chart depicting Shroom3 overexpression in PRCEC with PC-SHROOM3 transfection confirmed by RT-PCR and FIG. 13B by Western blot respectively (mean±SEM) [*p<0.05; p<0.001; *p<0.0001.

FIG. 14A is a graph depicting the results of Example 7 and showing the effect on TGF-beta induced expression of profibrotic matrix markers by RT-PCR. Shroom3 over-expression alone increased Collagen-1 and Fibronectin production while knockdown suppressed these matrix markers (mean±SEM) [*p<0.05; p<0.001; *p<0.0001]; FIG. 14B is a Western blot showing Shroom3 over-expression enhanced Phosphorylation of Smad-3 in response to TGF-beta in PRCEC at 15 minutes (Right); FIG. 14C is a photograph showing that TGF-β1 treatment of SHROOM3-overexpressed PRCEC also developed more prominent F-actin bundles compared to TGFβ1-treated cells without SHROOM3 overexpression (FIG. 14C-Upper and lower Panels).

FIG. 16A-16D: (16A) Representative genotyping results for ROSA-RTTA (upper) and COLTGM (lower) are depicted. (16B) Western blots of phospho-SMAD3 (p-SMAD3), total SMAD3 (SMAD3), Shroom3 and β-actin from mouse kidney cortex lysates from UUO kidneys of non-Dox-fed vs Dox-fed mice are displayed (n=2). (16C) Left to right—Photographs showing representative, low power (10×) images from Control kidney and UUO Kidney of non-Dox-fed animals, and UUO kidneys of Dox-fed animals are displayed. Upper row—Periodic acid Schiff stain, middle row—Picrosirius red stain. Lower row—immunolabelling for COL1A1 (TRITC-Alexa fluor) was performed on snap frozen kidney cortex sections. Representative images are displayed. Graph represents morphometric quantification of Area COL1A1 staining/total area (%) in 5 random high power fields per animal. (16D) Bar graphs depicting SHROOM3 and COL1A1 mRNA expression by RT PCR in control and UUO kidneys of DOX- and non-DOX fed animals (normalized to GAPDH; n=5; mean±SEM; ANOVA with post-test Bonferroni comparison; *P<0.05).

DETAILED DESCRIPTION OF THE INVENTION

Definitions

Figure 1:
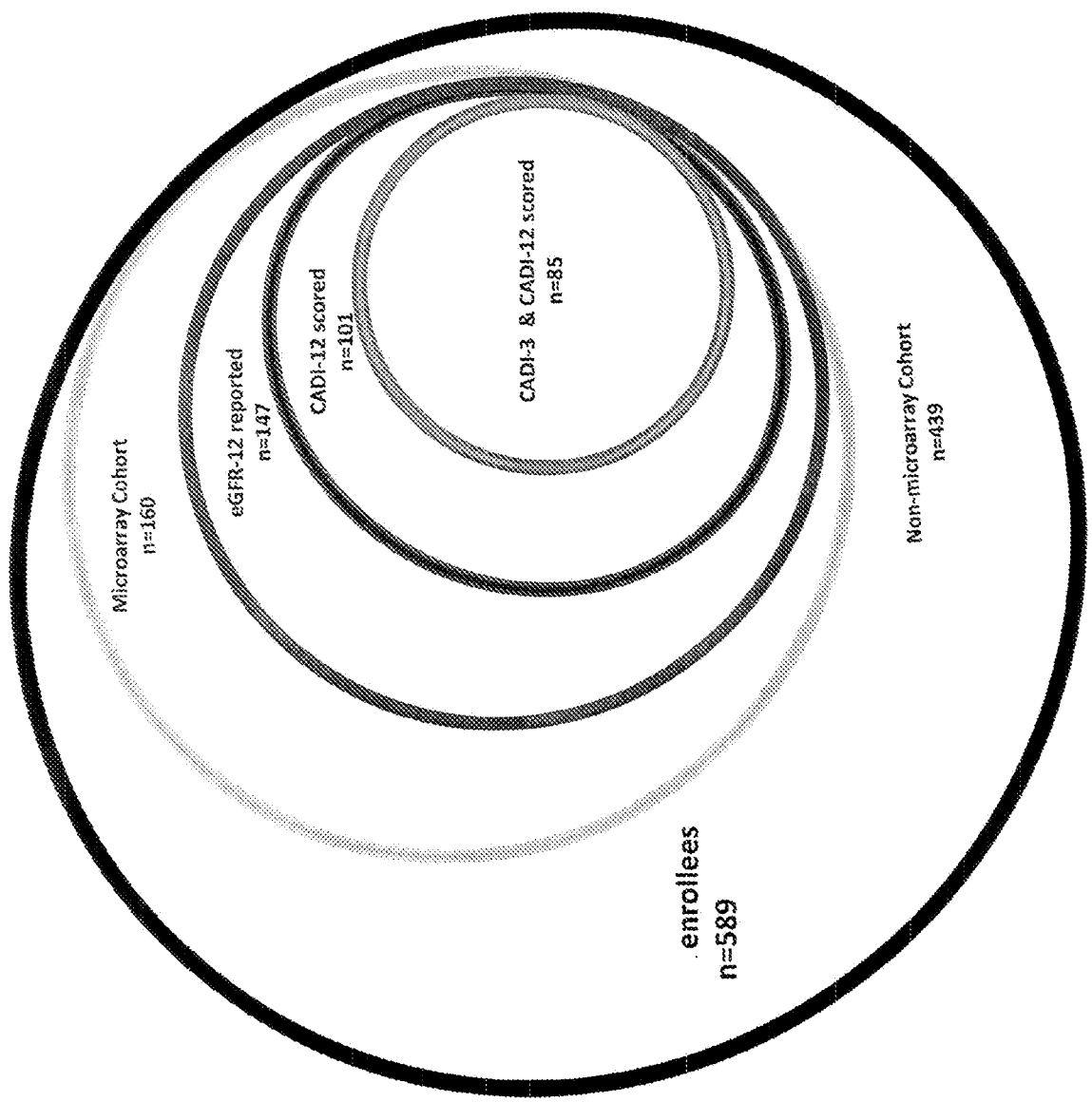
FIG. 1: a diagram depicting the number of participants in the study reported herein, and showing that 160 participants had 3-month allograft biopsy RNA extracted for microarray. Among these 160 patients, at 12-months post-transplant, 147 had eGFR-creatinine, 101 had CADI-12 and 85 had CADI-3 and –12 reported.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

The term "significantly higher levels of Shroom3 expression" is defined herein as between about 1.4 and about 5-fold higher than in the control.

The present invention is based on the discovery that the levels of SHROOM3 expression are significantly higher in kidney allograft recipients that are at risk for developing CAN when compared to control biopsies obtained normal subjects. Pursuant to the present invention, SHROOM3 expression levels are determined from biopsies obtained from kidney allograft recipients and compared to biopsies obtained from controls which are normal kidney samples such as living donor baseline biopsy samples or kidney samples from nephrectomy surgeries using techniques well known in the art such as immunostaining but preferably by Real Time Polymerase Chain Reaction (RT-PCR).

In a Genomics of Chronic allograft rejection study protocol, biopsies were obtained from all enrolled patients at different time points (See Examples below). From the DNA-microarray performed on allograft biopsies at 3-months, genes whose differential expression correlated with CADI-score and renal function at 12-months were identified and ranked. Among the top ranked genes in this list was SHROOM3 (Unpublished data).

Genome-wide association studies have also strongly linked a single-nucleotide polymorphism (SNP) in the SHROOM3 gene (rs17319721) with incident and prevalent CKD by eGFR in population-based cohorts of European ancestry {Kottgen A, 2009} {Boger C, 2011}. The SHROOM3 gene encodes a PDZ domain-containing protein that can directly bind F-actin and regulate its subcellular distribution in cells. Complete absence of, or defective SHROOM3 causes open neural tube defects and neonatal death in mice {Hildebrand J, 1999}. In MDCK kidney cell lines, SHROOM3 localizes at the apical and junctional complexes and is critical to the maintenance of normal epithelial cell phenotype {Hildebrand J, 2005}. It is also known that the C-terminal domain of SHROOM3 interacts with Rho-Kinases (ROCKs) to facilitate myosin phosphorylation and actin contraction {Nishimura T, 2008}.

In the study reported herein, 589 patients were enrolled. Allograft biopsies were obtained at 0, 3, 12, and 24 months post-transplant with Chronic allograft dysfunction index score (CADI) reported from a core lab. Gene expression microarray analysis was performed on 3 month biopsies (Affymetrix: human exon-1chip) and correlation to 12-month CADI and eGFR were analyzed (n=160). Overexpression and lentiviral suppression studies were performed on human primary tubular cells (RPTE). SHROOM3 gene-expression was found to correlate linearly with fibrosis and negatively with eGFR at 1 year (n=101; p<0.05). This was confirmed by RT-PCR independently (n=36). No correlation was seen between SHROOM3 expression and 3 month CADI (n=137).

A SNP in SHROOM3 (rs17319721) has been linked to CKD in genome-wide association studies. As disclosed herein, it has been found that the presence of at least 1 copy of the risk allele (i.e. A/G or A/A) in a donor's DNA is associated with higher intragraft SHROOM3 expression at 3 months (n=136; p=0.02). The risk allele was more prevalent in white vs. non-white donors. As shown in Example 4 below, the SNP risk allele is more frequent in white diabetics with renal disease. Therefore, the present invention provides a method for identifying the risk of developing CAN in a diabetic Caucasian patient suffering from renal disease that received a kidney from a donor, comprising the steps of obtaining a blood sample from the donor at baseline and conducting a genetic analysis to determine if the donor is homozygous for the risk allele. As shown in Example 9 below, the method can be practiced with non-diabetic Caucasian patients. If the donor is homozygous for the risk allele then the patient is at risk for CKD or CAN. This method can only be performed if the donor is available, which is not always the case. If the donor is not available then SHROOM3 expression levels in the patient can be examined. While in recipients of white-donor kidneys SHROOM3 expression was predictive of CADI at 12 months, this was not true for non-white or living donor recipients.

Overexpression of SHROOM3 in RPTE increased, while lentiviral suppression markedly diminished type-1 collagen production (p<0.01). SHROOM3 excess facilitated, while suppression inhibited canonical TGF-beta signaling, evidenced by Phospho-Smad3 and profibrotic marker production. Further, in FVB/N mice with CKD (HIV-nephropathy and Unilateral Ureteric Obstruction), SHROOM3 expression was increased compared to controls as determined by RT-PCR. Therefore, the present invention is not limited to CAN but is useful for other CKD such as obstructive uropathy, HIV-associated nephropathy and diabetic nephropathy.

Without wishing to be bound by theory, it is believed that Shroom3 is involved in any disease that involves fibrosis such as liver fibrosis and lung fibrosis. Therefore, the materials and methods described herein will be useful for monitoring the progression of such diseases. As shown below in Example 10 renal interstitial fibrosis was significantly abrogated in Shroom3 knockdown animals in a mouse model. These results validate the role of SHROOM3 in these diseases.

The present invention also provides kits for use in the methods disclosed herein. The kits comprise, in separate containers, the following components: primers for RT-PCR SHROOM3 expression assays, a microarray for gene expression analysis and primers for RT-PCR analysis of the rs17319721 risk allele, buffers and instructions for use. A non-limiting list of primers for use in the Kits is set forth in Table 5. The positive control comprises the cells overexpressing SHROOM3 or brain tissues, such as neuroepithelium, which are known to have high levels of SHROOM3 expression. (Shroom3-mediated recruitment of Rho kinases to the apical cell junctions regulates epithelial and neuroepithelial planar remodeling—Tamako Nishimura and Masatoshi Takeichi, Development 135, 1493-1502 (2008) doi: 10.1242/dev.019646).

The present invention is directed to methods for identifying kidney allograft recipients who are at risk for developing kidney diseases such as CAN or CKD. When such patients are identified, the present invention includes methods for treating such patients. Such methods include, without limitation, administration of immunosuppressive drugs, i.e. a calcineurin inhibitor (CNI), such as cyclosporine or tacrolimus, or a less fibrogenic immunosuppressive drug such as mycophenolate mofetil (MMF) or sirolimus. Since patients who are identified as being at risk for developing CAN or CKD have impaired renal function and often suffer from hypertension, administration of an angiotensin converting enzyme inhibitor (ACEI) such as lisinopril or angiotensin II receptor blockade such as losartan, to such patients is within the scope of the present invention.

The present invention also provides methods using SHROOM3 as a target to screen for drugs useful for the treatment of CAN and CKD. The 293T cells transfected with the SHROOM3 A-allele/luciferase construct described in Example 5 below can be used in screening assays to identify drugs for the treatment of fibrotic diseases mediated by SHROOM3. The cells can be seeded in 96 well microplates, contacted with drug candidates and assayed for changes in luciferase activity. SHROOM3 activity (i.e., luciferase) at baseline will be measured, and inhibitors Quercetin and/or BC-21, can be used as positive controls.

As an alternative, the 293T cells will be treated with TGFB1 (5-10 ng/ml), a known up-regulator of SHROOM3 expression and these cells (with a higher baseline of SHROOM3 expression) are used in the screening assays. These assays can be developed in a high throughput format.

Primers for use in RT-PCR assays for the A allele and for generating luciferase reporter constructs are set forth in Table 5.

In summary, pursuant to the present invention, SHROOM3 has been identified as a novel candidate gene whose expression in the renal allograft precedes and predicts the derangement of renal function and TIF in CAN. Significantly higher allograft SHROOM3 levels can be used to predict histological progression of CAN. In addition, it has been discovered that these relationships are most predictive in recipients of white-donor kidneys. These findings confirm for the first time that the previously described CKD-associated SHROOM3 locus (rs17319721) {Kottgen A, 2009} {Boger C, 2011} mediates its effect through increased SHROOM3 expression. Finally, the in vitro studies described herein suggest a salutary role for SHROOM3 in canonical TGF-beta signaling and Collagen-1 production in renal tubular cells. Taken together, these findings demonstrate that SHROOM3 is a therapeutic target in both CAN and CKD and suppression of its level can be used to inhibit the progression of TIF and retard ESRD.

The present invention is described below in working examples which are intended to further describe the invention without limiting the scope thereof.

In the Examples below, the following Materials and Methods were used.

Biopsies and RNA Extraction:

Real-time, ultrasound-guided, renal allograft biopsies were obtained at 0, 3, 12, and 24 months post-transplant, at 3 of 5 clinical sites. Two Cores were extracted using 18G spring-loaded biopsy needles when possible. If a single core was obtained, preference was given to RNA extraction (QIAGEN-ALLprep kit, Valencia, Calif. USA) at the 3-month visit and to histological analysis at 12-months. Tissue for gene-expression studies was stored immediately in RNA-later and shipped at −20° C. to a genomics core facility.

Reverse Transcription:

Extracted biopsy RNA were reverse transcribed using Sensiscript single-step RT (Qiagen) and Oligo-DT primer (Qiagen) with starting total-RNA amount of 55 ng. Extraction samples with RNA concentrations <5 ng/mcl by nanodrop were not used. For in vitro studies we used Superscript-III (Invitrogen-Life technologies, Grand Island, N.Y.) with starting total RNA 500-1000 ng.

RT-PCR:

Intron-spanning primer sets were designed for Shroom3 using Primer-BLAST (NCBI) and PCR amplicons were confirmed by both melting curve analysis and agarose gel electrophoresis. Shroom3 expression was assayed in an internal and external cohort of patients by real-time polymerase chain reaction (RT-PCR) (Applied biosystems 7500 cycler).

Shroom3 SNP Analysis:

Targeted genotyping was performed for Shroom3 SNP (rs17319721) using Taqman SNP analysis assay (Cat No: 4351379 Applied Biosystems, Foster City, Calif.). DNA was extracted (QIAGEN-ALLprep kit, Valencia, Calif. USA) from pre-implantation biopsies or blood for donor SNP and from peripheral blood for recipient SNP assay. Automated analysis using Genotyping software from Applied Biosystems was performed (Applied Biosystems 7500 cycler).

Shroom3 Promoter-Enhancer Constructs and Luciferase-Reporter Assay:

Promoter Fragments Spanning-3000 Bases 5' of the Translation Start Site of SHROOM3 were PCR amplified using primer sets that optionally included twenty-four base-pair sequences of the intron-1 of SHROOM3 including the rs17319721 site containing either of the two alleles (A or 1.G) (Table-1). Restriction sites for KpnI were introduced in all forward primer and Hind III in the reverse ones. The PCR products were then cloned into luciferase reporter vector-pGL3 Basic (E-1751, Promega, Wis., USA) using Kpn I and Hind III sites. This generated 3 reporter plasmids—Promoter only, Promoter with either intronic-A or -G sequences.

Transient transfection of these constructs (1 mcg each) with Renilla luciferase reporter plasmid-pTL-TK (200 ng) was carried out in HEK293T-cells plated on 6-well plates at 80% confluence (Polyjet reagent, SignaGen labs, Rockville, Md.). After 24-hours, cells were lysed and protein extracted. Renilla and Luciferase activity was measured in lysates using dual luciferase assay system (PJK Germany) on microplate reader according to manufacturer protocol. Results were expressed and Luciferase: Renilla ratio.

Western Blotting:

Cells were lysed with a buffer containing 1% Triton, a protease inhibitor mixture and tyrosine and serine/threonine phosphorylation and phosphatase inhibitors. Lysates were subjected to immunoblot analysis using Rabbit anti-Shroom3 (a gift from Dr Jeffrey Hildebrand, Pittsburgh), anti-V5 tag antibody (R960-25, Invitrogen-Life technologies), Phospho-Smad3antibody (Rabbit polyclonal—pS423/425) and Smad-3 (Rabbit monoclonal Smad-3, #9523, from Epitomics, Burlingame, Calif.). Densitometry was performed as previously described {Gassman 2009}.

Overexpression Studies:

A human Shroom3 construct (Open Biosystems, Lafayette, Colo.) was cloned into mammalian expression vector PC-DEST40 (Invitrogen, Carlsbad, Calif.) with C-terminal V5 and Histidine tags using Clonase-II recombinase (Invitrogen). Electroporative transfection using Lonza Nucleofector Technology (Basic Nucleofector kit for Primary Mammalian Epithelial Cells, Program T20) was used to transfect primary renal cortical epithelial cells (PRCEC) as described previously {Jin Y, 2012}. Forced expression was confirmed in PRCEC by RT-PCR and Western blot with empty destination vector transfection as control. Profibrotic extracellular matrix markers were analyzed in PRCEC by Real-time polymerase chain reaction (RT-PCR). Effect of TGF-β treatment on matrix marker production in Shroom3-transfected cells was assayed in nutrient starved medium 36 hours after transfection. Phosphorylation of Smad-3 was measured at 5, 15 and 30 minutes of treatment with TGF-Beta.

Shroom3 SIRNA Suppression Studies:

Human Shroom3 short hairpin clones (Open Biosystems, Lafayette, Colo.) were tested for Shroom3 suppression by RT-PCR and Western blot in 293-T cells. The selected GFP-tagged hairpin was transfected into 293-T cells along with envelope plasmids (Polyjet reagent) to generate a mammalian VSV pseudotyped lentiviral expression construct. PRCEC were infected using this lentiviral construct and Shroom3 suppression was confirmed. For in vivo Shroom3 suppression in mouse, potent suppressive hairpin sequences were shortlisted using a sensor Ping-Pong assay capable of deciphering elaborate shRNA libraries (Mirimus inc, Long Island, N.Y.). Mouse podocytes were transduced with these sequences on a Mir30 lentiviral backbone and tested for Shroom3 suppression using RT-PCR and Western blot. Two sequences were selected for embryonic stem cell injection into mice to develop a Tetracycline-inducible Shroom3-ShRNA mouse model.

Characteristics of the Participants

Five hundred eighty nine recipients were enrolled in the study from 5 centers at the completion of enrollment for the study. The demographic and clinical characteristics of donors and recipients in the cohort are listed in Table-1. Demographics and clinical characteristics of patients included in microarray studies are detailed in Table-2.

Example 1

SHROOM3 is Upregulated and Associated with Progression of CAN

Figure 2A:
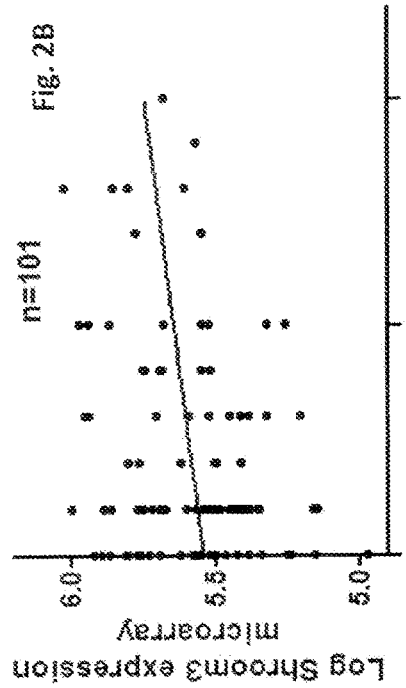
FIG. 2A-2D: graphs depicting (2A) the correlation of allograft log Shroom3 expression (microarray) at 3 months and eGFR creatinine at 12 months ($r=-0.20$; $p=0.007$); (2B) the correlation of allograft log Shroom3 expression (microarray) at 3 months and CADI-12 months (Pearson R—0.22; $p=0.027$; (2C) Shroom3 expression was higher in all donors with progressive fibrosis (Delta CADI=2 or more; n=17) vs those without significant progression (Delta CADI<2; n=68); and (2D) the correlation between 3-month Shroom3 expression was strongest in deceased-donor kidneys and 12-month CADI ($r=0.34$; $p=0.0088$) [Line represents mean; Whiskers=SD].
Figure 2B:
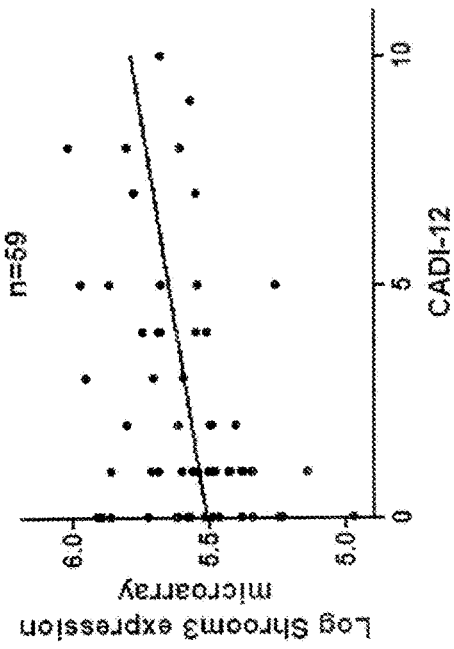
Figure 2C:
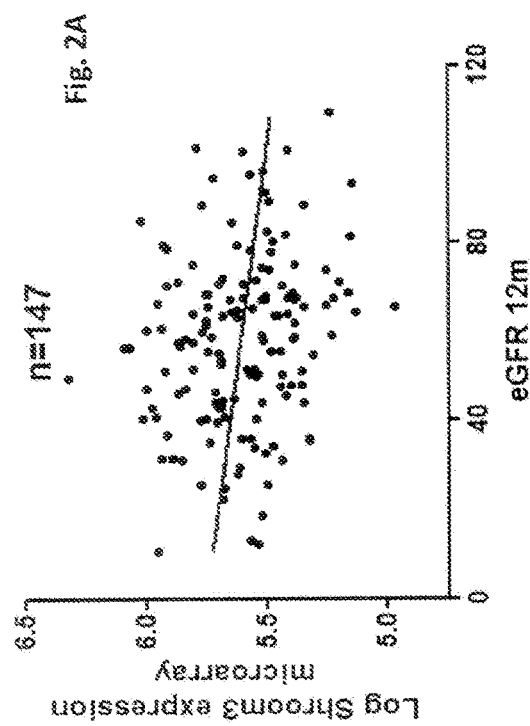
Figure 2D:
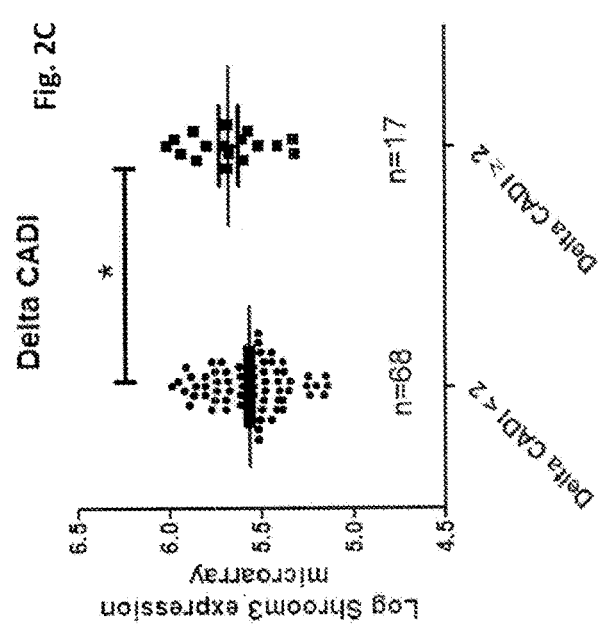

To identify genes that could potentially contribute to the development of CAN we performed an interim analysis for the first 66 subjects of the cohort who had the gene expression microarray data from the 3-month allograft biopsy as well as eGFR_12 and CADI_12. A list of candidate genes involved in CAN progression—that is, genes whose expression in the 3-month allograft sample correlated with a low eGFR_12 as well as a high CADI_12—were identified and ranked. SHROOM3 was among the top-ranked genes on the list (Table 3). Since the interim analysis, we have collected and analyzed additional samples. At the time of preparation of the instant application, 3-month allograft gene expression profiles have been performed on 160 allografts and of which 12-month eGFR (eGFR_12) was available in 147 subjects and 12-month CADI (CADI_12) was available in 101 subjects (FIG. 1). When we re-examined the correlation of 3-month allograft SHROOM3 expression in the 147 subjects who had eGFR_12 available, 3-month allograft SHROOM3 expression correlated inversely with eGFR_12 ($r=-0.2192$, $P<0.01$, FIG. 2A). Of the 101 subjects who had CADI_12, 3-month allograft SHROOM3 expression on gene expression microarray analysis correlated linearly with CADI_12 ($P=0.03$, FIG. 2B), which remained significant ($P=0.02$) when 2 of the allograft samples were excluded from the analysis—one with BK-virus nephropathy and another with cortical scarring. No correlation was identified, however, between 3-month allograft SHROOM3 expression and simultaneous 3 month CADI ($n=135$; $r=-0.1273$, $P=0.14$, (FIG. 3D). The relationships of 3-month SHROOM3 expression to CADI_12 and eGFR_12 were further validated by quantitative real-time polymerase chain reaction (qRTPCR) analysis in an internal cohort of 32 subjects ($r=-0.3873$, P=0.02 for eGFR_12 and r=0.3774, P=0.03 for CADI_12, (FIGS. 3C & 3D). We also found a robust correlation between microarray and qRTPCR SHROOM3 expression (n=32, r=0.5613; p=0.0008, (FIGS. 2B and 2C). The relationship between Log-SHROOM3 expression and 12m-CADI was strongest in DDRs (p<0.01)(FIG. 2D). In multivariate analysis only cold-ischemia time and presence of acute rejection had significant effect on CADI_12. SHROOM3 expression remained significant in deceased donors (p=0.02). Of the 160 subjects who had 3-month allograft SHROOM3 expression examined by microarray, 85 had both 3- and 12-month CADI scores available. To further corroborate that SHROOM3 expression is associated with progression of CAN we compared SHROOM3 expression between allografts that had ≥2 increase in CADI score (n=17; progressors) to those with less than <2 increments (n=68; non-progressors) between 3- and 12-month biopsies. SHROOM3 expression was significantly higher in progressors compared to non-progressors (p=0.04).

Example 2

Association of SHROOM3 and CAN Progression Exists in Caucasian-Donor Allografts

Figure 4A:
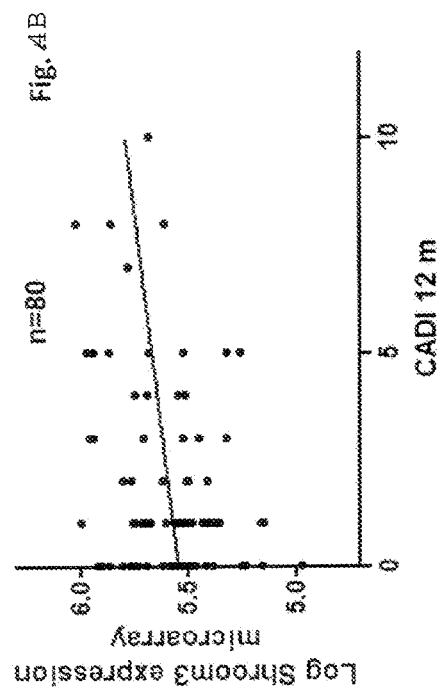
Figure 4B:
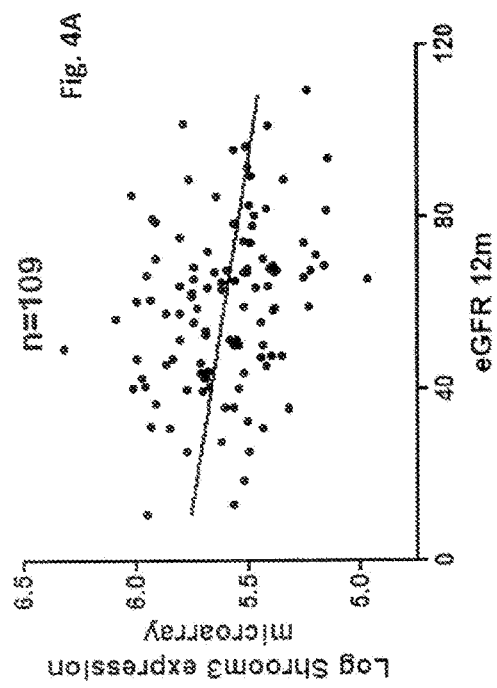
Figure 4C:
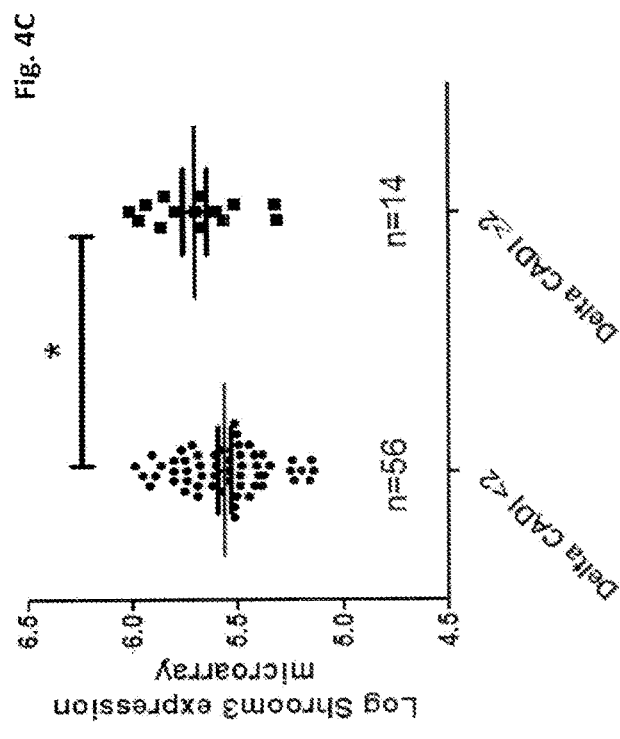

Since a genetic variant of SHROOM3 (SNP variant rs17319721) is associated with CKD when studied in predominantly Caucasian cohorts [Kottgen A, 2009], we sought to determine whether the relationship observed between SHROOM3 and CAN followed a racial predilection. Of the 147 allografts with available eGFR_12, 109 were from Caucasian donors and their SHROOM3 expression was inversely correlated with eGFR_12 (r=−0.2712, P=<0.01, FIG. 4A). Among 101 allografts with available CADI_12, 80 were from Caucasian donors and SHROOM3 expression in those allografts significantly correlated with CADI_12 (P=0.02, FIG. 4B). In non-Caucasian allografts, SHROOM3 expression was not significantly correlated to either eGFR_12 (n=38) or CADI_12 (n=21) (FIG. 5B, 5C). Among the 85 patients with CADI_3 and CADI_12, 70 received Caucasian-donor kidneys. In them, we compared Shroom3 expression between progressors and non-progressors. SHROOM3 expression for the 14 allografts that developed ≥2 increments in CADI was significantly higher those with <2 change in CADI (n=56) (FIG. 3C). SHROOM3 expression in the 3-month allograft biopsy was also significantly different between allografts with varying severity of CAN based on CADI_12: low (CADI 0-1; n=49), intermediate (CADI 2-5; n=24), high (CADI>5; n=7) (P=0.03, FIG. 3C).

Example 3

Figure 6B:
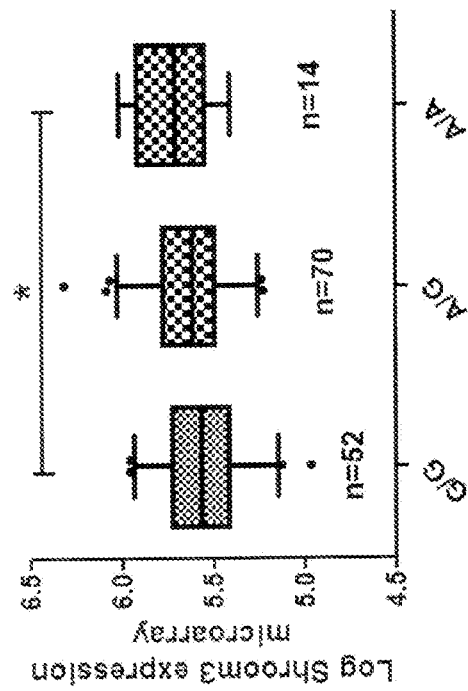
FIG. 6A-6B: graphs illustrating that (6A) Shroom3 SNP (rs17319721) is differently distributed between whites and non-whites (amongst both donors and recipients). Whites have a higher prevalence of effect allele ($p<0.0001$) (6B): Homozygosity for the risk allele in donor kidneys is associated with significantly increased allograft Shroom3 expression ($p=0.033$) whiskers: 5th-95th percentile; Line at Median; $p=0.0183$) [*$p<0.05$; $p<0.001$; *$p<0.0001$]
Figure 6A:
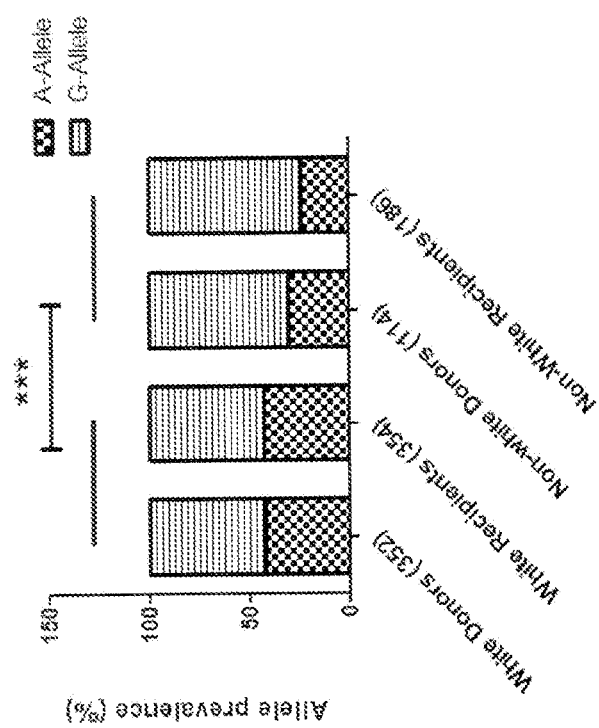

A Non-Coding SHROOM3 Variant in the Donor is Associated with Increased SHROOM3 Expression The A-allele (minor allele) of a non-coding SHROOM3 SNP at rs17319721 has been strongly linked to chronic kidney disease by eGFR-creatinine [Kottgen A, 2009; Boger C, 2011]. We performed targeted SNP genotyping for the rs17319721 variant in 540 allograft recipients and 468 donor samples. Allelic prevalence of the risk allele (A) was 36.66% among recipients and 40.02% among donors. In both recipients and donors, we observed that the prevalence of the risk allele was significantly higher in Caucasians compared to non-Caucasians (P<0.0001) (FIG. 6A). Since a higher SHROOM3 expression correlates with CAN progression and the risk allele of SHROOM3 is associated with CKD in predominantly Caucasian cohorts, here we examined whether allograft SHROOM3 expression correlated with the presence of the risk allele. Of the 160 allografts for which SHROOM3 expression was available, targeted SNP genotyping of the rs17319721 variant was performed in 136 cases where either donor blood samples or pre-perfusion allograft biopsy samples were available. SHROOM3 expression was significantly higher in allografts that were homozygous for the risk allele (A/A, n=14) compared to allografts that were homozygous for G allele (G/G, n=52, P=0.01, FIG. 6B). SHROOM3 expression of A/G-allografts (n=70) was not significantly different from A/A or G/G. However, SHROOM3 expression was significantly higher in allografts from donors with at least one risk allele (A/A or A/G; n=84) compared to donors without the risk allele (G/G; n=52, P=0.02). When specifically examined in 103 Caucasian-donor allografts and 33 non-Caucasian-donor allografts the relationship between SHROOM3 expression and the risk allele in the allograft remained constant but did not attain statistical significance (P=0.05 in Caucasian-donors FIGS. 7A & 7B respectively). Interestingly, when we examined the relationship of SHROOM3 expression to recipient-genotype rather than the donors, there was no significant correlation between risk allele and expression in 147 recipients (FIG. 7C).

Example 4

Figure 8B:
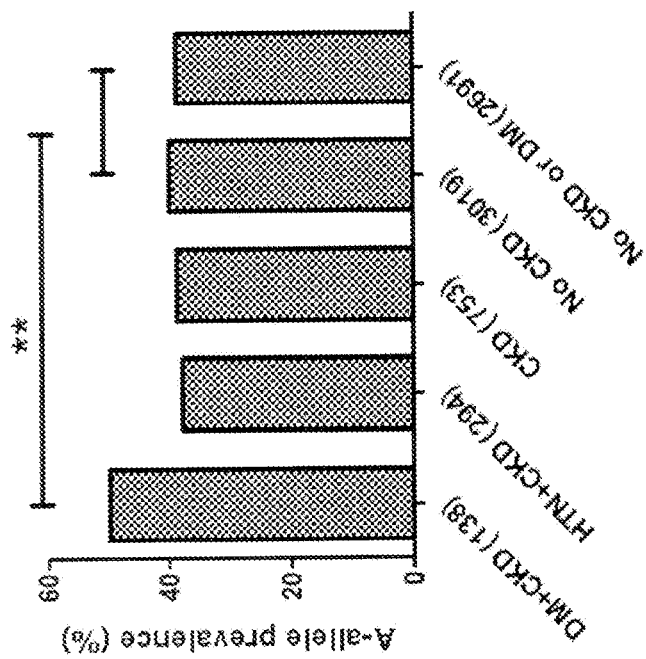
FIG. 8A-8B: graphs that illustrate (8A) Allele prevalence of the Shroom3 SNP in 354 white recipients (as %) according to ESRD etiology. Recipients with ESRD from Diabetes (49%) had the significantly greater risk-allele prevalence compared to unrelated donors. (8B): Allele prevalence of the Shroom3 SNP in 3247 patients of the study. Risk allele prevalence was highest in Diabetics with CKD (51%) [*$p<0.05$; $p<0.001$; *$p<0.0001$].
Figure 8A:
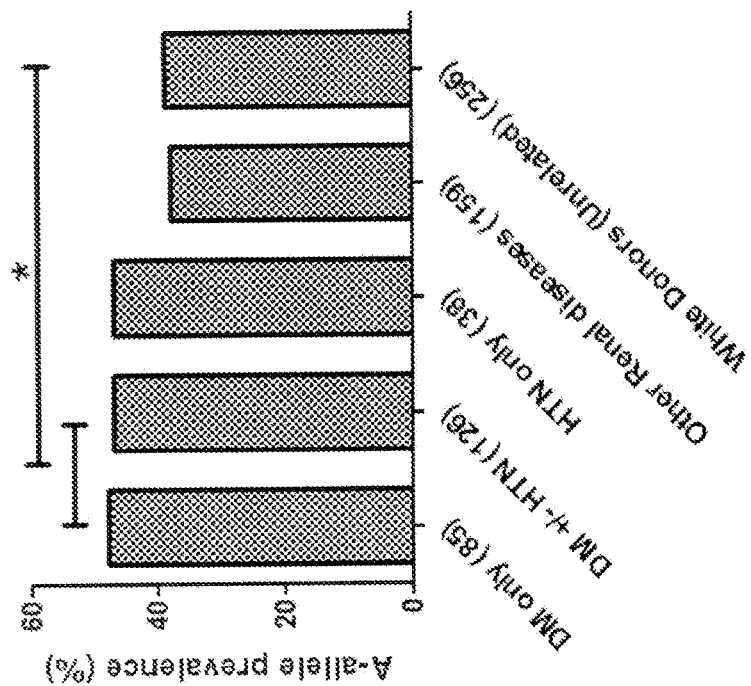

Risk Allele of SHROOM3 is Associated with Diabetic Mellitus as the Cause of ESRD and CKD in Caucasians Since the risk variant of SHROOM3 has been linked to CKD, we examined whether the risk allele is associated with a particular etiology ESRD in our cohort of recipients. As the risk allele of SHROOM3 was differently distributed between the different ethnicities (Tables 4a & 4b), we have restricted all subsequent comparisons between donors and recipients to the same ethnicity. We observed that the allelic frequency of the risk allele was not significantly different between Caucasian donors and recipients (42.87% vs. 43.07% respectively). As only 114 of the 468 donors were non-Caucasians, the number of subjects in each non-Caucasian ethnicity (i.e. AAs, Asians, Hispanics and others) was insufficient to make valid inference about SHROOM3 genotype and its relationship to ESRD etiology. When we analyzed the allele prevalence among Caucasian recipients according to their documented ESRD diagnosis (excluding recipients who had previous transplants, congenital diseases, or unknown etiology of ESRD), we noted that the risk allele was most prevalent in Caucasian recipients with diabetes mellitus as their primary ESRD diagnosis (47.25%; n=126). We found that Caucasian recipients with diabetes alone without hypertension had an unadjusted odds ratio of 1.418 (95% CI=1.000-2.11; p=0.04) while patients with diabetes with hypertension had an odds ratio 1.36 (95% CI=1.031-1.814; p=0.029) of having the risk allele when both were compared to all Caucasian donors who were not related to the recipients (FIG. 8A). Furthermore, the allelic prevalence for the risk allele in patients with diagnosis other than diabetes and HTN as causes for ESRD was 38.36% (n=159), which was not significantly different from allelic frequency in unrelated allograft donors (39.64%). For external validation of the association of the risk allele with diabetic kidney disease, we analyzed an independent cohort of subjects. Among the Caucasian participants of the study (n=3782), 763 were identified as having CKD. Again allele prevalence was significantly higher in those with Diabetes and CKD (n=138) compared to those without CKD (n=3019) and, those without CKD or Diabetes (n=2691) (50.4% vs. 40.4% vs 39.3%, P<0.01) (FIG. 8B). In multivariate analysis within the Caucasian cohort using age, BMI, hypertension, diabetes, family history of diabetes or kidney disease as covariates, adjustment for diabetes negated any effect of the risk allele on CKD as an outcome. The allele prevalence was also similar in non-diabetics with and without CKD (38.6% vs 39.26% respectively). Within the CKD cohort, AAs with CKD (n=721) and, Diabetes with CKD (n=204) had similar allele distribution as those without CKD (n=2729) (20.59% vs 18.46% vs 21.78%; P=0.8159) suggesting that the SHROOM3 SNP does not play a significant role in diabetic/non-diabetic kidney disease in this group.

Example 5

Figure 9:
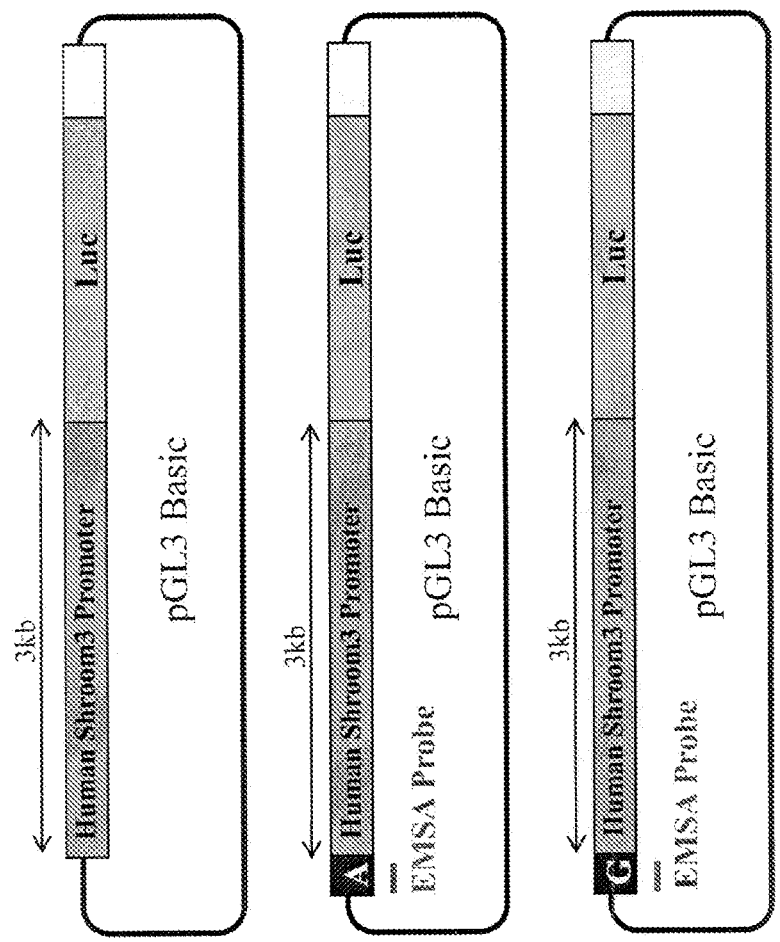
FIG. 9: a construct map of Luciferase-reporter plasmids used in Example 5 below.
Figure 10B:
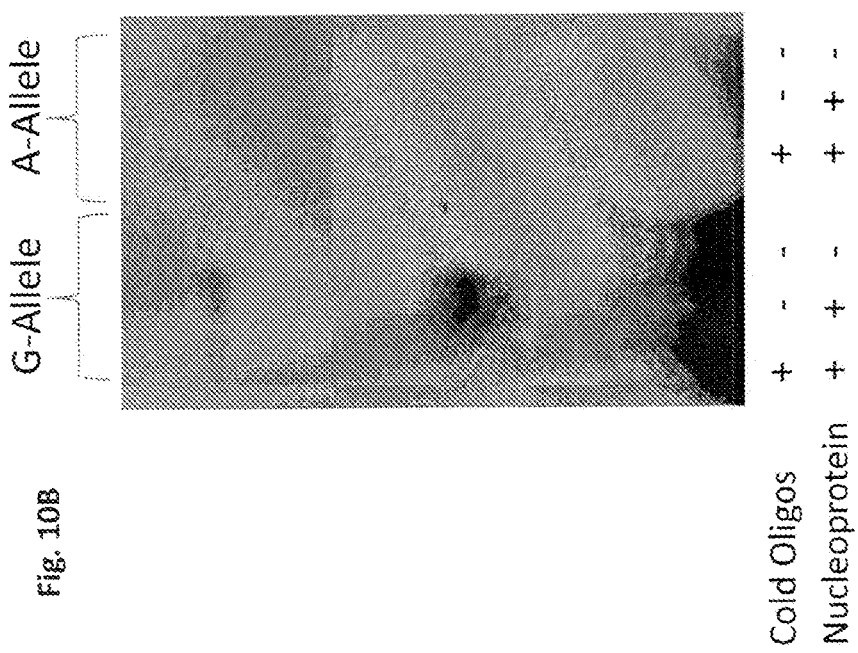
FIG. 10A-10B.
Figure 10A:
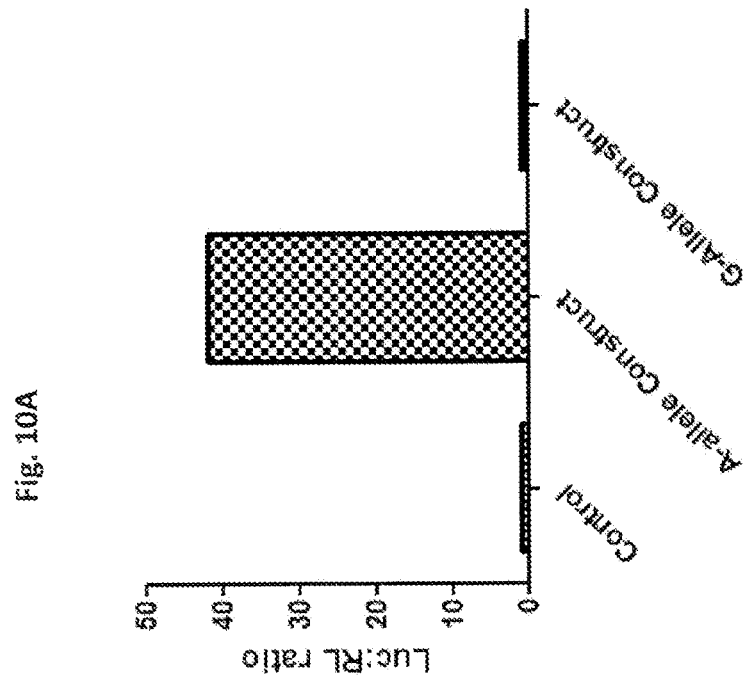

Risk-allele of rs17319721 enhances SHROOM3 expression through TCF4-mediated transcriptional activation rs17319721 is located within the first intron of SHROOM3. Since the A allele is associated with a higher expression of SHROOM3, we sought to understand the effect of the G-to-A substitution on the transcriptional regulation of SHROOM3. When we examined the intronic region of SHROOM3 containing rs17319721, we found that the G-to-A substitution generates a potential consensus binding sequence for transcription factor 4 (TCF4/TCF7L2), a high mobility group (HMG) box-containing transcription with the consensus binding sequence of 5'-(A/T)(A/T)CAAAG-3'. TCF4 is involved in the Wnt/β-catenin signaling pathway [Wortman B, 2002; Henderson U, 2012]. Additionally in our microarray analysis, patients in the highest quartile of Shroom3 expression also had significantly upregulated TCF7L2 and Beta-Catenin (P<0.0001). To further examine whether this intronic region containing the rs17319721 SNP possesses any function as an enhancer of SHROOM3 transcription, we generated two SHROOM3 promoter-enhancer luciferase reporter constructs that consisted of a 3 Kb SHROOM3 promoter region and a 100bp sequence from the first intron of SHROOM3 containing either the A-allele or the G-allele of the rs17319721 (FIG. 9. Construct maps). The SHROOM3 reporter construct with the A-allele had a higher increase in luciferase-to-renilla reporter activity compared to the G-allele without TGFβ stimulation and with TGFβ stimulation there was an increase in activity. Treatment with either a TCF4 inhibitor, BC21, or a β-catenin inhibitor Quercetin, abrogated the difference in reporter activity between the A- and G-allele reporter constructs (FIG. 10A) which further confirmed that TCF4-enhancer sequence is responsible for the difference in the expression of the A-vs G-allele reporter constructs. To further confirm TCF4 binding to the 100-bp SHROOM3 intronic region we performed EMSA. TCF4 binding to the intronic sequence containing the A-allele was more than the G-allele, which was abrogated in samples with excess cold oligos (FIG. 10B)

Example 6

TGFβ1 Enhances SHROOM3 Expression in a β-Catenin/TCF4-Dependent Manner

Figure 11A:
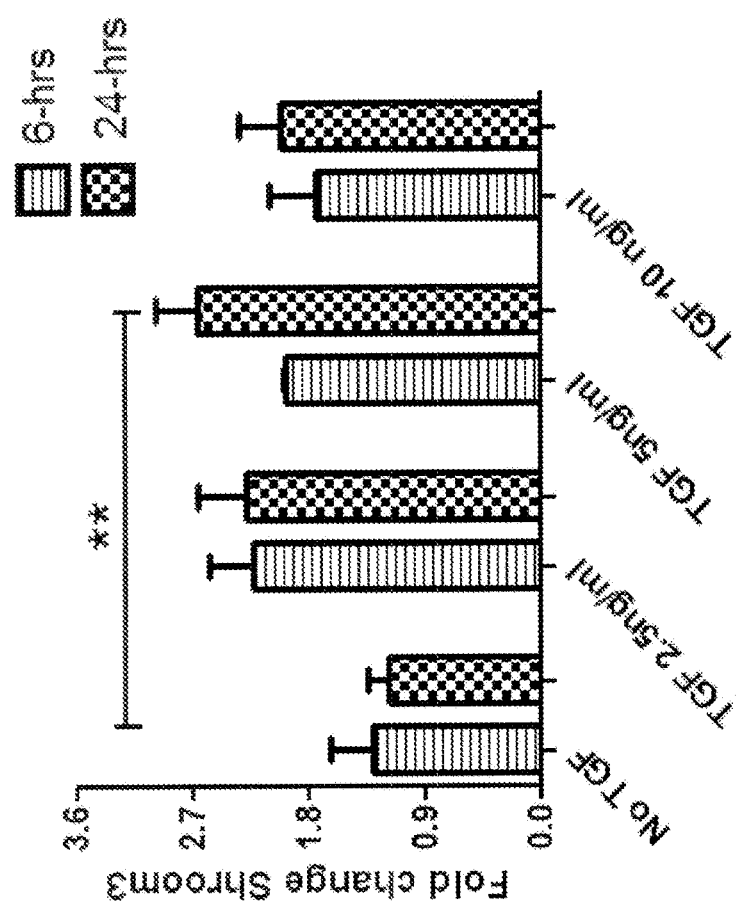
FIG. 11A-11B.
Figure 11B:
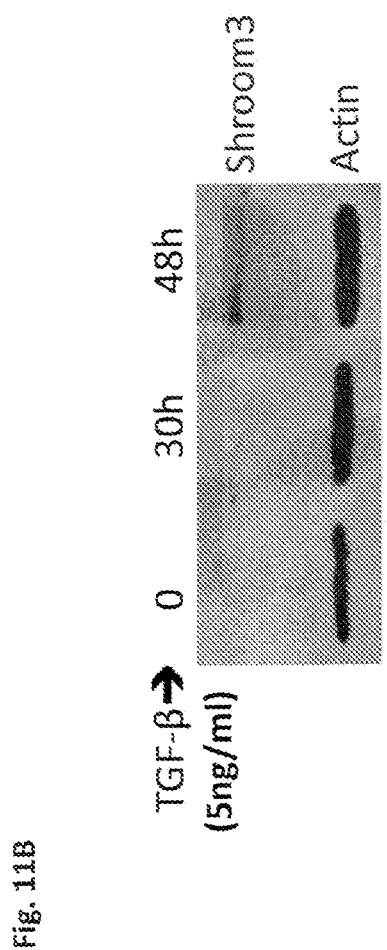
Figure 12A:
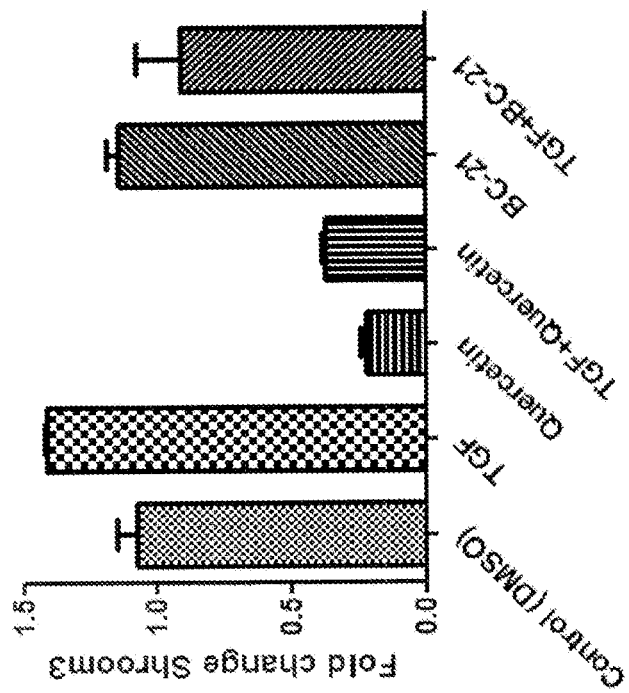
FIG. 12A-12B.
Figure 12B:
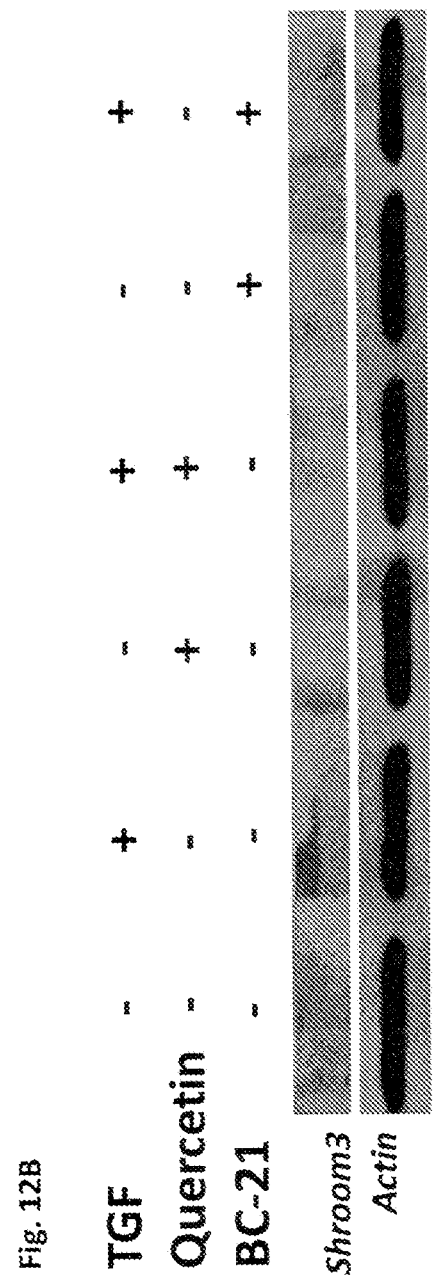

Since SHROOM3 is regulated by TGFβ1 in HK-2 cells [Brennan E P, 2012] and TGFβ1 is a key growth factor mediating renal injury and fibrosis [Ian H Y 2012] we further characterized TGFβ1-mediated regulation of SHROOM3. We found that TGFβ1 treatment of PRCEC increased SHROOM3 mRNA expression maximally at 5 ng/ml (FIG. 11A) and protein expression at 48 hours (FIG. 11B). Analysis of the SHROOM3 promoter sequence—up to −10 kb from the transcriptional start site—using a transcription factor binding motif prediction program (TRANSFAC) did not reveal any Smad-binding sequence, suggesting that the TGFβ1-induced increase in SHROOM3 expression is not due to canonical TGFβ1/SMAD signaling. As TGFβ1 is known to crosstalk with the Wnt/β-catenin/TCF4 pathway and TCF4 regulates SHROOM3 expression, we tested whether TGFβ1-induced SHROOM3 expression is dependent on β-catenin/TCF4 interaction. We found that both BC-21 and quercetin abrogated the TGFβ1-induced increase in the expression of SHROOM3 protein (FIG. 12A) and mRNA (FIG. 12B), thus confirming that TGFβ1-induced SHROOM3 expression is β-catenin/TCF-4 dependent.

Example 7

Figures 13A, 13B:
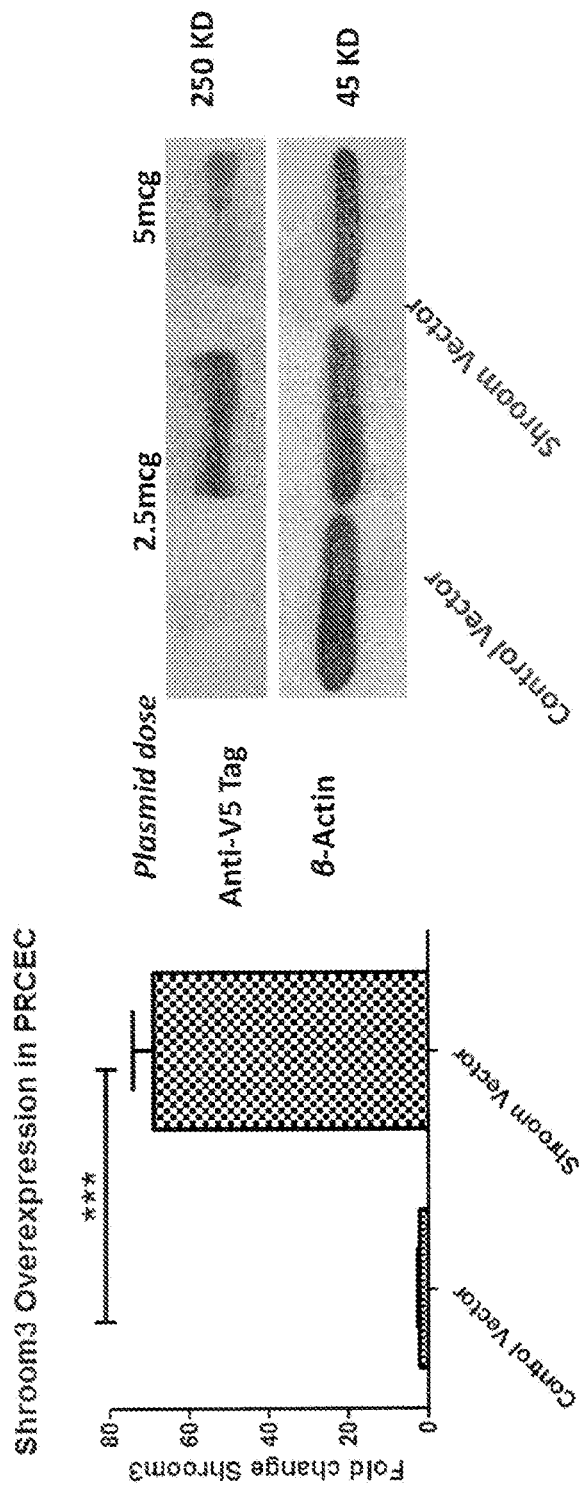
FIG. 13A-13B.
Figure 14A:
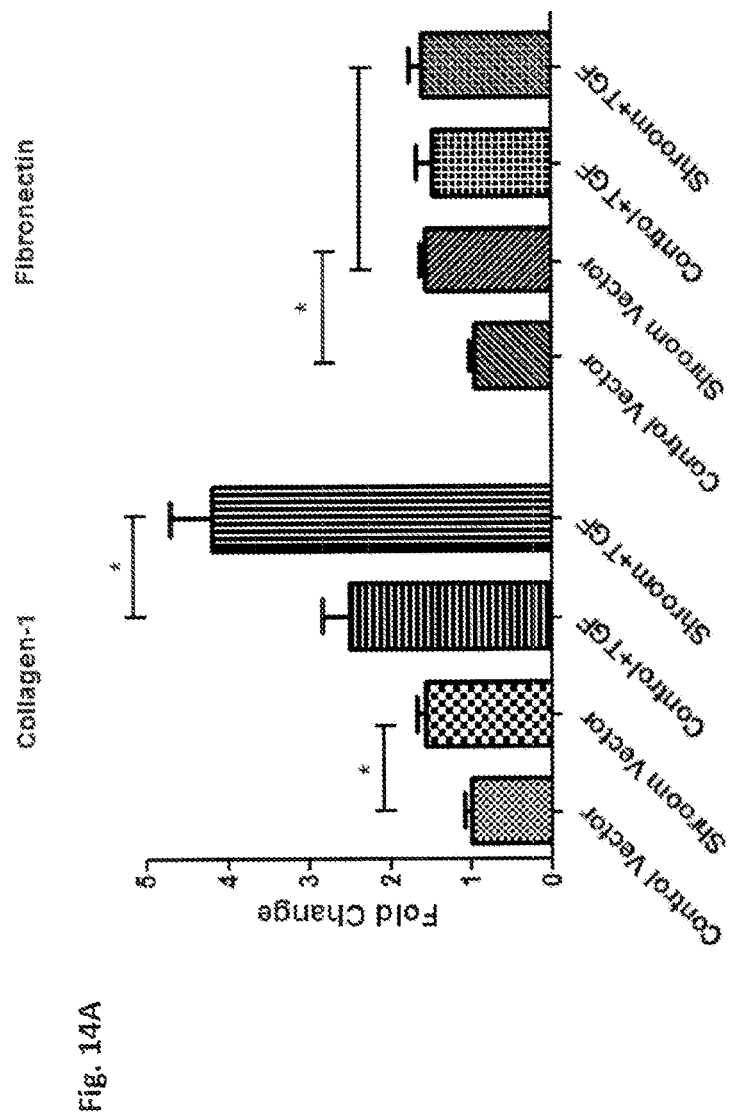
FIG. 14A-14C.
Figure 14B:
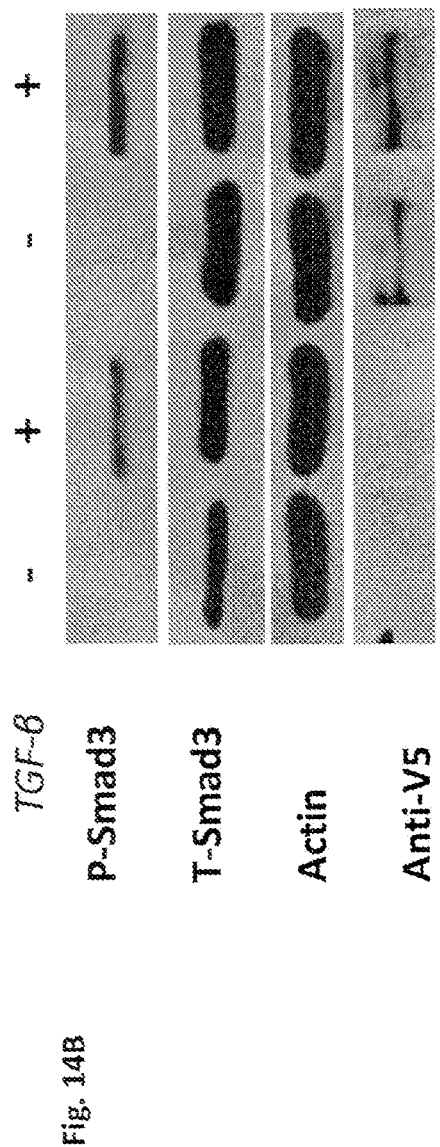
Figure 14C:
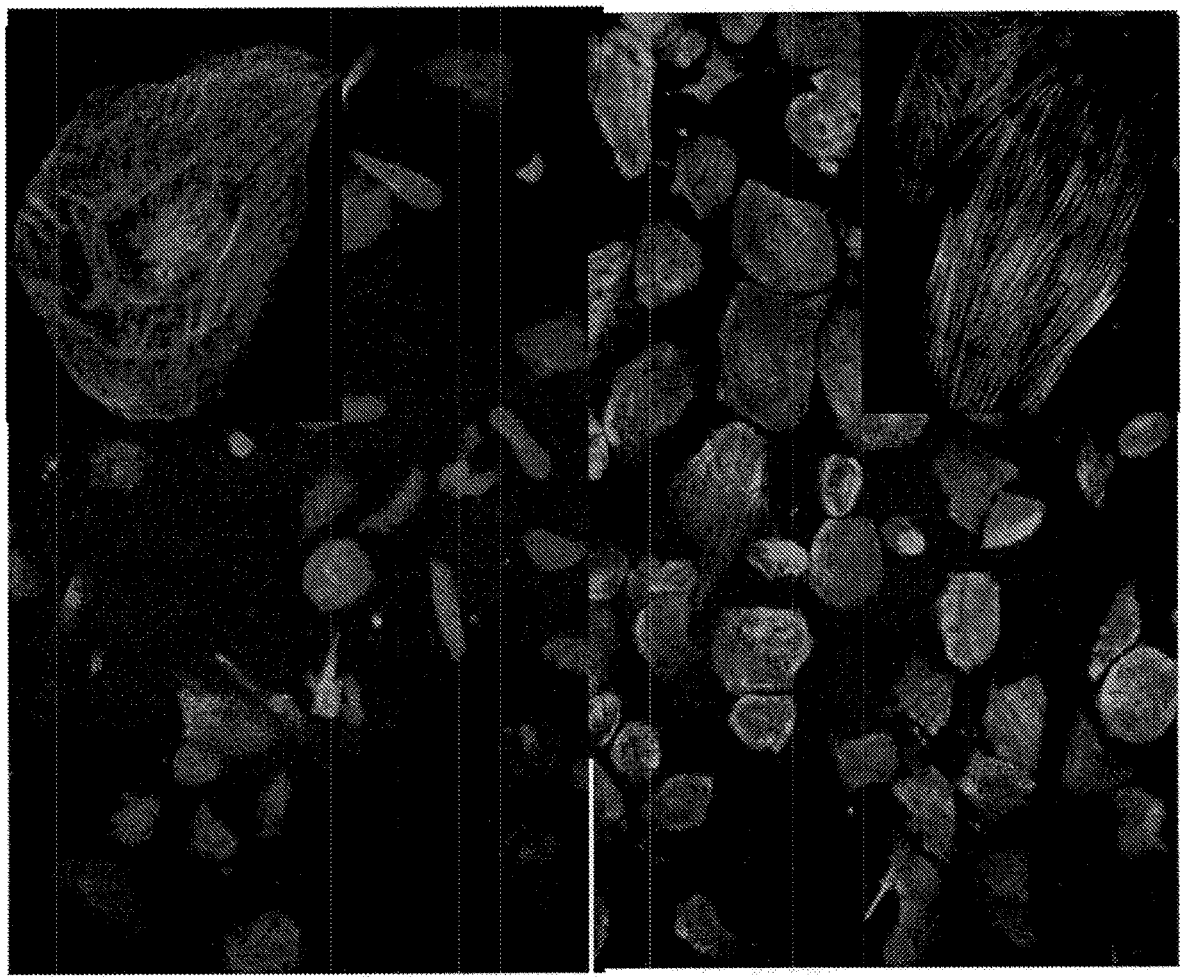
Figure 15A:
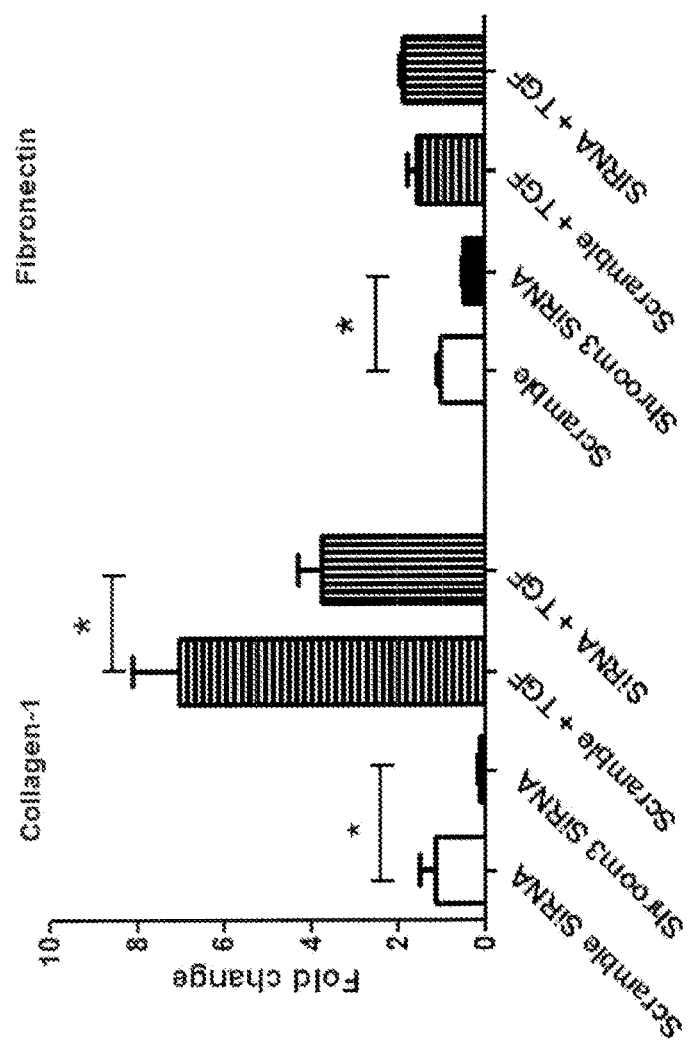
FIG. 15A-15B: Graphs that depict the results of Example 7 which establishes that Shroom3 overexpresses in PRCEC with PC-SHROOM3 transfection, confirmed by RT-PCR (FIG. 15A) and Western blot (FIG. 15B) respectively (mean±SEM) [*p<0.05; p<0.001; *p<0.0001]
Figure 15B:
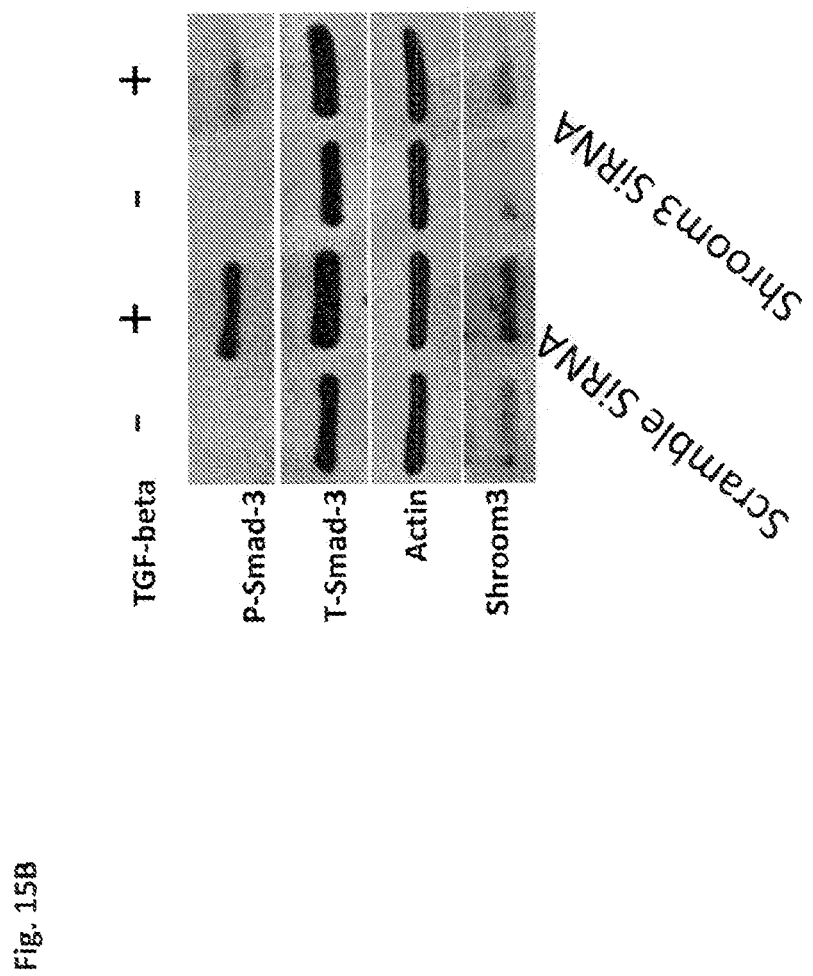

SHROOM3 Facilitates Canonical TGFβ1/SMAD3 Signaling and Profibrotic Gene Expression We investigated whether SHROOM3 has any impact on TGFβ1-mediated pro-fibrotic gene program, which is a well-characterized driver of kidney fibrosis in CKD as well as CAN [Lan H Y 2012; Campistol J M 2001]. First we compared the expression of TGFβ1-target genes related to tissue fibrosis in PRCEC with or without SHROOM3 overexpression that were treated with either TGFβ1 or vehicle. Overexpression of SHROOM3 was confirmed by RTPCR (FIG. 13A) and Western blot (FIG. 13B). The expression of profibrotic TGFβ1-target genes, including COL1A1 and FN1, were increased by TGFβ1 treatment alone as well as SHROOM3 overexpression alone (FIG. 14A). TGFβ1-induced expression of COL1A1 was further increased in cells with SHROOM3 overexpression compared to those without SHROOM3 overexpression (Vector+TGF). To further characterize how SHROOM3 facilitated TGFβ1 signaling we investigated the phosphorylation of SMAD-3 which indicates activation of canonical TGFβ1/SMAD signaling in PRCEC. Cells with or without SHROOM3 overexpression were treated with either TGFβ1 or vehicle. Phosphorylation of Smad3 in TGFβ1-treated cells was enhanced by SHROOM3 overexpression compared to vector-transfected cells (FIG. 14B). TGFβ1 treatment of SHROOM3-overexpressed PRCEC also developed more prominent F-actin bundles compared to TGFβ1-treated cells without SHROOM3 overexpression (FIG. 14C—Upper and lower Panels). Next, we sought to determine whether TGFβ1-induced profibrotic gene program is dependent on SHROOM3. SHROOM3 knockdown in PRCEC significantly reduced COL1A1 and FN1 transcripts (FIG. 15A). TGFβ1-induced expression of COL1A1 was also significantly attenuated in SHROOM3 knockdown cells compared to cells transduced with the empty lentivector. TGFβ1-induced expression of FN1, however, was not affected by SHROOM3 knockdown. Phosphorylation of SMAD3 in SHROOM3-knockdown cells was significantly reduced at 30 min, but not at 15 min, after TGFβ1 stimulation compared to cells without SHROOM3 knockdown (FIG. 15B). When taken together these results suggest that SHROOM3 facilitates TGFβ1/SMAD3-induced pro-fibrotic gene expression program. Further supportive of this was our finding in the microarray cohort of CTGF, Vimentin, Collagen-IV (downstream of TGF/SMAD3 signaling) were among genes significantly upregulated in patients in the highest quartile of SHROOM3 expression.

Example 8

A-Allele of Rs17319721 in the Donor is Associated with Higher Allograft SHROOM3 Expression at 3 Months Multiple studies have now linked the rs17319721 Shroom3 SNP to CKD20-22. Whether the risk allele is associated with altered SHROOM3 expression in the renal parenchyma, or is related to CAN is not known. As of Jan. 1, 2013, five hundred eighty nine recipients have been enrolled in the parent study. We performed targeted genotyping for this locus on 540 allograft recipients and 517 donors within our cohort. Allelic prevalence of the CKD-associated A-allele was 36.66% among recipients and 39.94% among donors. Overall, the prevalence of the A-allele was similar for Caucasian donors and recipients (42.87% vs. 42.56% respectively). The number of subjects in each non-Caucasian ethnicity (i.e. AAs, Asians, Hispanics and others) was not sufficient to make valid inference about rs17319721 distribution. In both recipients and donors, we observed that the prevalence of the A-allele is significantly higher in Caucasians compared to non-Caucasians (P<0.0001).

Next, we examined whether allograft SHROOM3 expression at 3-months (SHROOM3-3M) correlated with the presence of the A-allele. Allograft gene expression microarray analysis from 3-month protocol biopsies was performed on 159 out of the entire 589 enrollees in this study. These patients represent by chronology the first 159 enrollees who were biopsied 3 months after transplantation. Both targeted genotyping results for rs17319721 and SHROOM3-transcript levels from kidney allografts were available from 136 donors and 145 recipients. We observed that SHROOM3-3M was significantly higher in allografts that were homozygous for the CKD risk allele (A/A, n=14) compared to allografts that were homozygous for the G allele (G/G, n=52, P=0.01). SHROOM3-3M was also significantly higher in allografts from donors with at least one risk allele (A/A or A/G; n=84) compared to donors without the risk allele (G/G; n=52, P=0.02). Interestingly, when we examined the relationship of SHROOM3-3M with respect to the recipient's genotype, rather than the donor's, there was no significant correlation between the A-allele and SHROOM3-3M (n=145).

Example 9

Allograft SHROOM3 Expression at 3-Months and A-Allele of Rs17319721 are Associated with Higher Risk of CAN in Renal Allograft Recipients Since we observed that the A-allele of rs17319721 is associated with SHROOM3 transcriptional activation and, that increased SHROOM3-expression facilitated TGF-β1 signaling in PRCEC, we examined whether SHROOM3-3M and/or the donor risk-genotype correlated with indices of allograft dysfunction (CAN) at 12-months.

Allograft gene expression microarray analysis from 3-month protocol biopsies was performed on 159 out of the entire 589 enrollees in this study. At the time of this filing, eGFR-12 was available in 147 subjects and CADI-12 was available in 101 subjects from the subgroup. Reasons for not having a 12-month biopsy in this subgroup included graft loss (n=8), death (n=1), lost-to-follow up (n=9), contraindication for or inability to obtain a renal allograft biopsy (n=40).

SHROOM3-3M correlated inversely with eGFR-12 (r=−0.2192, P<0.01) and positively with CADI-12 (r=0.2458, P=0.03). This correlation remained significant (P=0.01) after exclusion of 2 biopsies with diagnosis (BK-virus nephropathy and severe cortical scarring). The relationship between SHROOM3-3M and CADI-12 was stronger in deceased-donor allografts (p<0.01). The relationships of SHROOM3-3M to CADI-12 and eGFR-12 were further validated by qRTPCR in an internal cohort of 32 subjects (r=−0.39, P=0.02 for eGFR-12 and r=0.38, P=0.03 for CADI-12). A robust correlation existed between SHROOM3 expressions from microarray and qRTPCR (P=0.0008). No correlation existed, however, between SHROOM3-3M and simultaneous 3-month CADI (n=135). SHROOM3-3M was predictive of CADI-12 greater than 2 (CADI-12≥2) and inversely related to eGFR-12 in multivariate analysis. Among covariates included in the analysis, acute rejection before 3 months had significant independent effects on CADI-12, and on eGFR-12 (P<0.05).

To corroborate that SHROOM3-3M is associated with progression of CAN we compared SHROOM3-3M between allografts that had ≥2 increase in CADI score (ΔCADI≥2, n=17, known as Progressors) to those with less than <2 change in CADI score (ΔCADI<2, n=68, known as Non-progressors) between 3- and 12-month biopsies. To minimize the effect of baseline disease on subsequent histological progression, we excluded allografts with CADI-3>2 from this analysis. SHROOM3-3M was significantly higher in the Progressors compared to the Non-progressors (P=0.04).

Next we examined the donor risk genotype and its association with CAN. At the time of analysis, two-hundred and three subjects of the cohort have had CADI scores reported at 12 months—101 from the microarray cohort and 102 from the non-microarray cohort. In this group, the presence of the A-allele in the donor was associated with a significantly greater risk of a CADI-12≥2 in all allografts (OR=1.98, CI=1.10-3.59), indicating a higher risk of CAN with the risk allele.

Example 10

Figure 16A:
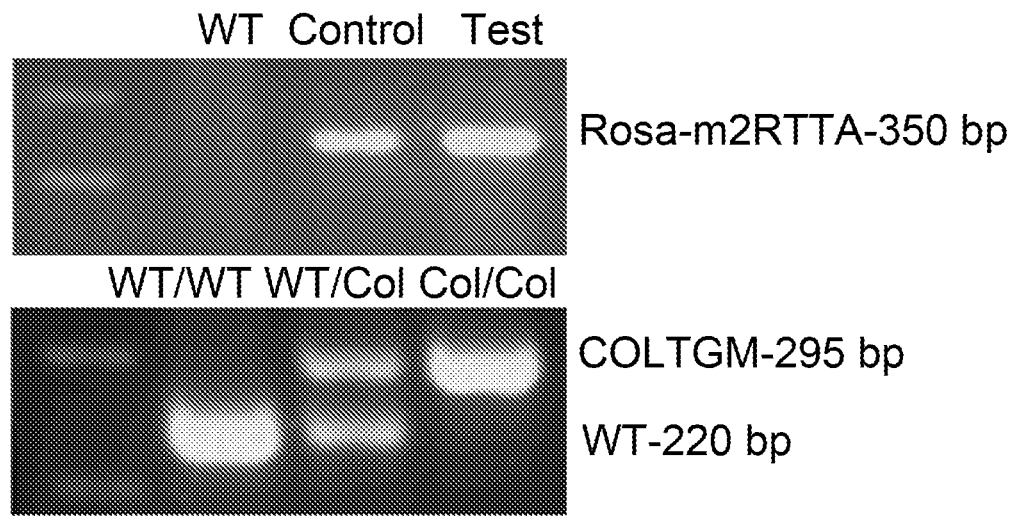

SHROOM3 Facilitates Canonical TGF-β1/SMAD3 Signaling and Profibrotic Gene Expression in a Murine Model In Vivo Methods To examine the mechanism of facilitation of fibrosis by SHROOM3, we developed a murine model of inducible shRNA-mediated SHROOM3 knockdown. In our model, reverse tetracycline-controlled transactivator (RTTA)-elements were linked to the universal ROSAm26 promoter for RTTA expression in all cell-types. After in vitro validation, two SHROOM3-specific shRNA hairpins were linked to doxycycline-RTTA-responsive elements and positioned 3' to the Collagen-1 gene. Sample genotyping PCR for Rosa-RTTA element and shRNA (COLTGM) sequences and southern blot gel electrophoresis are displayed (FIG. 16A). Doxycycline (DOX) feeding to induce Shroom3 knockdown in genotyped mice was initiated 3-weeks prior to UUO surgery and continued until the date of sacrifice 10-days later. To study the development of renal interstitial fibrosis, we performed unilateral ureteric obstruction surgery (UUO) on 8-10 week old animals after 3-weeks of DOX-feeding (n=5 in each shRNA clone). Mice were sacrificed at 10-days post UUO. SHROOM3-shRNA animals of the same age that were not fed with DOX were used as controls. Results were analyzed quantitatively by the unpaired t-test.

Results

Figure 16B:
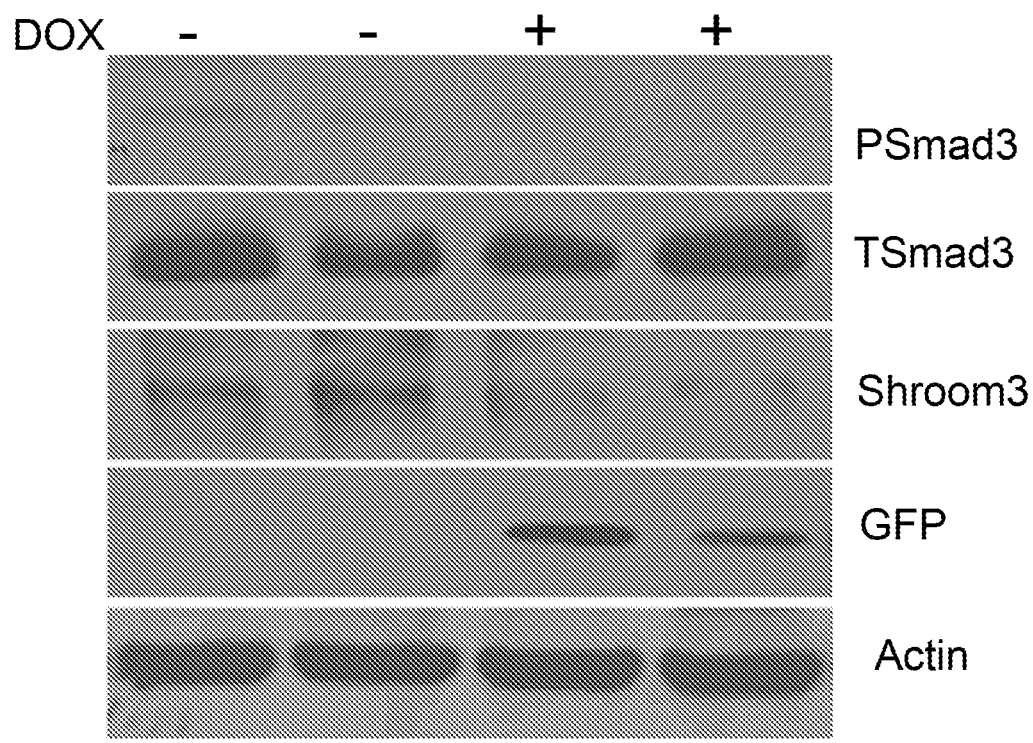
Figure 16C:
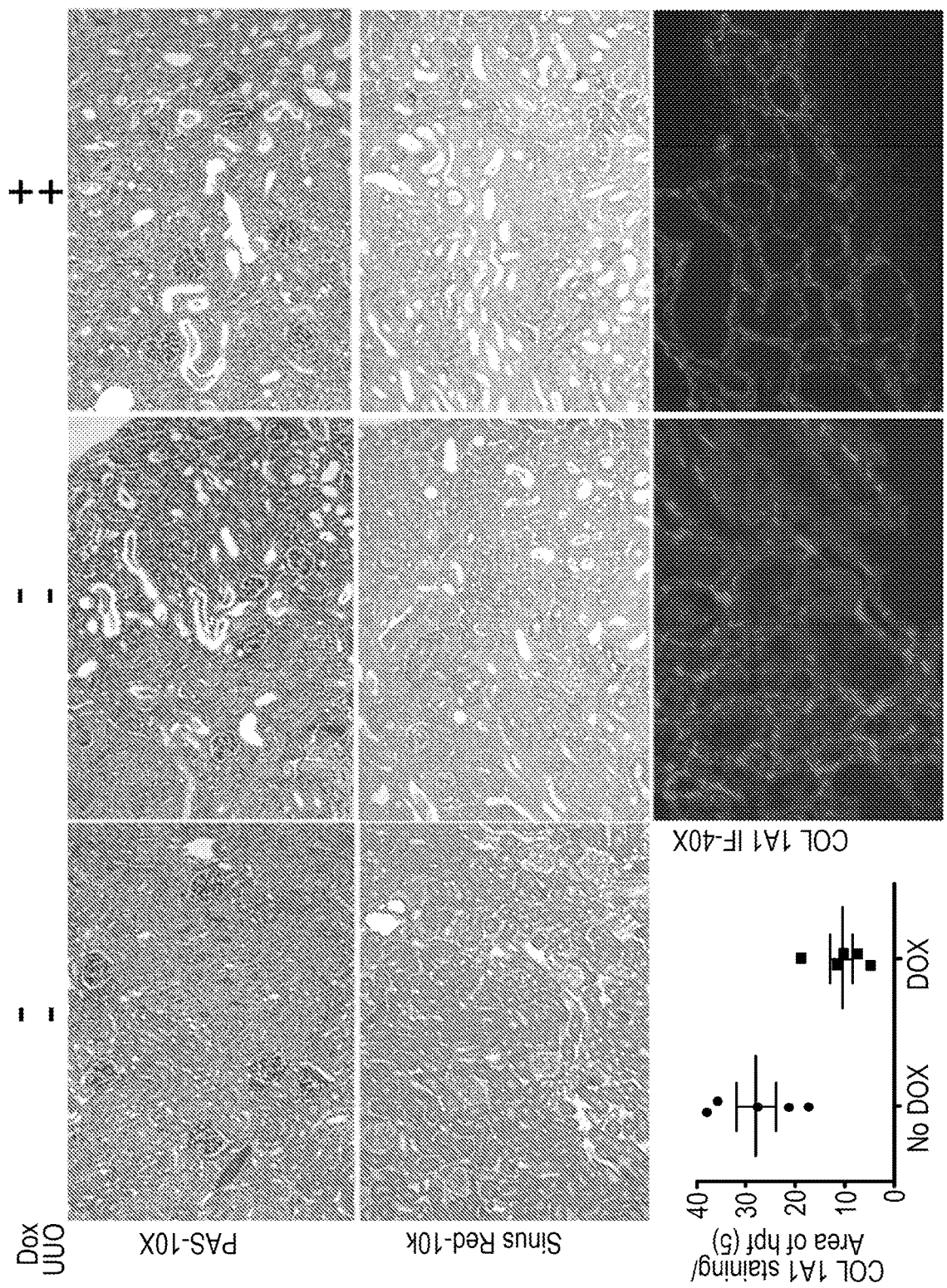

We examined the impact of shRNA-mediated SHROOM3 knockdown on TGF-β1/SMAD3 signaling and renal fibrosis in the above DOX-inducible shRNA mouse strain. Doxycycline (DOX) feeding of these animals confirmed SHROOM3 knockdown (~75%) by 3-weeks (real-time PCR (RT-PCR) and Western blot (WB) from renal cortical lysates (FIGS. 16B and 16D). DOX-fed animals showed significantly inhibited phosphorylation of SMAD3 in UUO kidneys by Western blot (FIG. 16B). COL1A1 production in UUO kidneys was inhibited with Shroom3 knockdown as shown by RTPCR of kidney lysates and by immunofluorescence (IF) in tissue sections (FIG. 16C—lower panel and graph; and 16D). Renal interstitial fibrosis measured by picrosirius red staining (FIG. 16C—middle panel), was significantly abrogated in Shroom3 knockdown animals. These results validate the role of SHROOM3 in canonical TGF-β1 signaling.

Discussion

Chronic allograft nephropathy remains a substantial cause for allograft failure and RRT {Paul L C, 1999} {Chapman J R, 2005} {Racusen L C, 2010} {USRDS 2012}. Modern immunosuppressive strategies have had significant impact on short term allograft outcomes with much less improvement in long-term outcomes {Hariharan S, 2000} {Meier-Kriesche H U, 2004} {Lamb K E, 2011}. Further, CAN remains a histological entity with arbitrary stages and variability between reporting pathologists {Solez K, 2008} {Akalin E, 2010} {Ying L, 2009} {Halloran P, 2002}. Therefore, identification of newer markers for potential early diagnosis and therapy of CAN is imperative. In the GoCAR study, we are examining the ability of allograft gene-expression profiles from protocol biopsies at 3-months to predict the development of CAN and TIF at 12 months. We thus identified Shroom3 as a novel candidate gene whose allograft expression precedes and predicts the derangement of renal function and the progression of TIF.

While evolved CAN has shown distinct transcriptional signatures in prior studies {Flechner S, 2004} {Donauer J, 2003}, issues have been raised regarding their interpretation and generalizability. Development of biomarkers and/or therapeutic strategies has been impeded by large gene-panel sizes, small sample sizes, single time point biopsies, heterogeneity of gene chip assay used and low fidelity of pre-array amplification techniques {Ying L, 2009} {Akalin E, 2010}. Studies based on for-cause biopsy transcriptional profiles are less reliable for developing predictive panels or therapeutics for CAN due to gene diversity dependent on pathology at the time of biopsy. To determine a gene-signature that would predict the development of CAN, Scherer et al, profiled amplified RNA (Affy HG-U95Av2 chip) from 6-month protocol biopsies of 17 patients, 12 of whom went on to develop CAN. They developed a 10-gene cluster that was 88% predictive of developing chronic rejection at 12-months. The relationship however, was not significant when single genes were analyzed {Scherer A, 2003}. We used unamplified RNA from 3-month biopsies and whole-exon gene chip array (~4 probes/exon, ~40 probes/gene) to correlate differentially expressed genes with eGFR and CAN at 12 months in our larger cohort of patients. Furthermore, Shroom3 expression in our study retained its significance when analyzed alone in the entire cohort with better correlation in the subset of DDRs and WDKRs. This was validated in our smaller internal-external cohort of patients by RT-PCR. Importantly, mean Shroom3 transcript levels were significantly higher in patients whose CADI-scores progressed (Delta CADI≥2) between 3 and 12 months compared to those with relatively stable histological scores. This implies a role for Shroom3 in the progression of fibrosis and CAN.

TIF is a common histological end-point for CAN and CKD. Consequently, genes linked to fibrogenesis and EC-matrix production, specifically related to TGF-beta signaling, have emerged as differentially regulated from transcriptional studies in patients with CAN and animal models of CKD {Flechner S, 2004} {Hotchkiss H, 2006} {Mas V, 2007} {Ju W, 2009}. A SNP in Shroom3 has emerged independently linked to incident and prevalent CKD in Caucasian predominant cohorts {Kottgen A, 2009} {Boger C, 2011}. However, Shroom3 gene function and its relationship to loss of eGFR and TIF are hitherto unknown. In PRCEC, our RT-PCR studies suggest a small but significant overproduction of EC-matrix markers (Collagen-land Fibronectin) by Shroom3 overexpression and a marked suppression of these markers with SiRNA mediated Shroom3 inhibition. Further, Shroom3 overexpression appears to facilitate canonical TGF-beta signaling as evidenced by enhanced Smad-3 phosphorylation in PRCEC. Consistent with this is the amplified response of profibrotic marker production (SNAIL, MMP-2, collagen-1) upon TGF-beta treatment in Shroom3-transfected cells compared to controls. Also in line with these observations are the suppressed P-Smad3 and Collagen-1 levels we observed with Shroom3 SiRNA in TGF-treated cells. TGF-beta also increased Shroom3 expression in PRCEC. Other groups have made this observation in HK-2 cells using RNA-sequencing {Brennan E P}. This along with the salutary effect of increased Shroom3 on TGF-beta signaling may indicate a positive feedback loop between Shroom3 and TGF. Together, these suggest that higher Shroom3 expression may have profibrotic effects in renal epithelial cells. Interestingly, from our biopsy data, having one or two copies of the risk-allele (A) in the donor appears to significantly increase Shroom3 transcript levels in biopsy tissue (~1.4 fold). There was no consistent association between recipient-SNP and Shroom3 expression suggesting little contribution of allograft Shroom3 expression from infiltrating recipient cells. In summary, this implies that the association between the SNP and CKD in prior GWAS studies may be explained by increased kidney Shroom3 levels and a subsequent profibrotic response that go along with having the risk allele.

In univariate analysis the association between Shroom3 expression and eGFR/CADI was significant in WDKRS and DDRs but not in non-WDKRs or LDRs. Notably, of the DDRs, 51/59 were WDKRS. The effect-allele prevalence was also significantly higher in whites compared to non-whites in our analysis. Prior GWAS studies that identified Shroom3 involved Caucasian predominant cohorts {Kottgen A, 2009} {Boger C, 2011}. In a study to identify susceptibility loci for Urinary-albumin creatinine ratio (UACR), the Shroom3 SNP retained association to eGFR and UACR in whites but did not attain significance in African-Americans {Ellis J W, 2011}. Our observation of the lack of association between Shroom3 expression and eGFR/CADI in non-whites is similar to these published results. The increased Shroom3 expression with the presence of the A-allele in the donor, however, was also observed in non-WDKRs. Further the mean Shroom3 expression by microarray was not significantly different between WDKRs and non-WDKRS (data not shown). Hence, the insignificant effect of Shroom3 on eGFR/CADI in non-whites is unclear. Non-WDKRs in the microarray (n=21) and RT-PCR (n=5) were fewer than WDKRs. More conjecturally, a polymorphism having greater impact on allograft outcomes in non-WDKRs that we did not analyze may be differently distributed within this cohort. In the cohorts reported on herein—European-Americans with diabetic ESRD and CKD respectively had the highest prevalence of the risk allele of rs17319721. However, the Family Investigation of Nephropathy and Diabetes (FIND) study did not report linkage between loci on chromosome 4 and diabetic nephropathy in Caucasians {Igo R P, 2011}. The inconsistency between these results may stem from our comparison group which included only kidney donors who were not related.

All patients in the 3-month microarray did not have biopsies for outcome assessment at 12-months (17 allograft losses, 42 lost follow-up or refused 12-month biopsy). The sample size of 101 patients is still robust in comparison to prior transcriptional studies in allograft recipients {Flechner S, 2004} {Donauer J, 2003} {Sarwal M, 2003} {Reeve J, 2009}. Only 36 patients had sufficient quality RNA for RT-PCR validation after microarray-though the relationships were significant within this sample. While the facilitation of TGF-beta signaling by Shroom3 excess was observed in vitro, the mechanism of this interaction is uncertain. The C-terminal ASD-2 domain of Shroom3 has been shown to be essential for Rho-Kinases 1&2 (ROCKs) recruitment and function in the invaginating neural tube. Mutation of this domain leads to loss of ROCK-function {Nishimura, 2008}. In chondrocytes, ROCKs facilitated and ROCK-inhibitor (Y27632) inhibited Smad3-phosphorylation with TGF-beta treatment {Xu T, 2012}. Further, in animal models of unilateral ureteral obstruction, ROCK-inhibitors retarded renal interstitial fibrosis and GFR-decline {Satoh S, 2002} {Nagatoya K, 2002} {Takeda Y, 2010}. Though we did not test this, the mechanism of interaction with TGF-beta may in part be through Shroom3-mediated ROCK facilitation. Finally, the rs17319721 locus on the Shroom3 gene is intronic, between exons 1 and 2. The reason for the apparent regulatory effects of this region is less clear from our observations. Recently, the results from the Encyclopedia of DNA elements (ENCODE) consortium have been sequentially published describing the regulatory functions attached to intronic loci within the human genome {Dunham I, 2012} {Neph S, 2012} {Gerstein M, 2012}. Studies using histone methylation mapping suggest that the Shroom3 SNP is located in an area predicted to have enhancer function {Dr Katalina Susztak, ASN 2012}. This is consistent with our findings.

In summary, Shroom3 is a novel candidate gene whose expression in the renal allograft precedes and predicts the derangement of renal function and TIF in CAN. Higher allograft Shroom3 levels appear to predict histological progression of CAN. We also show that these relationships are best in recipients of white-donor kidneys and deceased-donor kidneys. Our findings confirm for the first time that the previously described CKD-associated Shroom3 locus (rs17319721) {Kottgen A, 2009} {Boger C, 2011} mediates its effect through increased Shroom3 expression. Finally our in vitro studies suggest a salutary role for Shroom3 in canonical TGF-beta signaling and type I collagen production promise as a therapeutic target in both CAN and CKD to reduce the progression of TIF and retard ESRD.

The present invention also includes a kit for use in identifying patients suffering from kidney diseases and for predicting the progression of kidney fibrosis and TIF in renal allograft recipients. The kit consists of reagents for RT-PCT analysis of Shroom 3 expression and a microassay for detecting the rs 17319721 SNP risk allele, a positive control for the RT-PCR assays, buffers and instructions for use. The kit is used by obtaining a renal biopsy from a patient who received a kidney transplant from a donor, determining Shroom 3 expression and comparing a level of Shroom 3 expression in biopsy specimen with the level of Shroom 3 expression in the positive control in the kit, all by RT-PCR. The microarray is used to identify kidney donors who are homozygous for the Shroom 3 A allele.

TABLE 1

Demographics of GOCAR enrollees

| Demographics | N (%) | Mean ± SD [range] |
|---|---|---|
| Recipient Age: All Recipients | 589 | 50.17 yrs [18-83] |
| Recipient Gender (Percent females) | 185 (31.41) | |
| Recipient Race: | | |
| White (W) | 375 (63.37) | |
| African-American (AA) | 123 (20.88) | |
| Asian (A) | 34 (5.77) | |
| Hispanic (H) | 34 (5.77) | |
| Other (O) | 16 (2.71) | |
| Recipient ESRD diagnosis-All recipients: | | |
| Diabetes only | 115 (19.42) | |
| Hypertension only | 97 (15.28) | |
| Diabetes & Hypertension | 90 (15.28) | |
| Polycystic disease | 53 (8.99) | |
| Glomerular disease (including FSGS/IgA) | 107 (18.17) | |
| Unknown | 16 (2.72) | |
| Prior transplants | 13 (2.38) | |
| Others | 98 (16.64) | |
| Donor Age | 589 | 42.01 yrs [0-76] |
| Donor Gender (Percent females) | 278 (47.20) | |
| Donor Race: | | |
| White (W) | 451 (76.57) | |
| African-American (AA) | 57 (9.68) | |
| Asian (A) | 17 (2.89) | |
| Hispanic (H) | 45 (7.64) | |
| Other (O) | 19 (3.23) | |
| Donor type: | | |
| Deceased-Donors (DD) | 329 (55.86) | |
| Living-Related Donors (LRD) | 147 (24.96) | |
| Living-Unrelated Donors (LURD) | 113 (19.19) | |
| Donor SNP analysis | 468 | |
| Recipient SNP analysis | 540 | |

TABLE 2

Demographics of patients in the microarray studies (CADI & eGFR analysis)

| Demographics | N (%) | Mean ± [range] |
|---|---|---|
| Recipient Age | 160 (100) | 48.64 ± 13.27 yrs [19-73] |
| Recipient Gender (Percent females) | 47 (29.35) | |
| Recipient Race: | | |
| White (W) | 92 (57.5) | |
| African-American (AA) | 37 (23.1) | |
| Asian (A) | 10 (6.25) | |
| Hispanic (H) | 14 (8.75) | |
| Other (O) | 7 (4.38) | |
| Donor Age | 160 | 41.13 ± 16.80 yrs [3-76] |
| Donor Gender (Percent females) | 77 (48.13) | |

TABLE 2-continued

Demographics of patients in the microarray studies (CADI & eGFR analysis)

| Demographics | N (%) | Mean ± [range] |
|---|---|---|
| Donor Race: | | |
| White (W) | 121 (75.63) | |
| African-American (AA) | 17 (10.63) | |
| Asian (A) | 7 (4.38) | |
| Hispanic (H) | 12 (7.5) | |
| Other (O) | 3 (1.88) | |
| Donor type: | | |
| Deceased-Donors (DD) | 95 (59.38) | |
| Living-Related Donors (LRD) | 35 (21.88) | |
| Living-Unrelated Donors (LURD) | 30 (18.75) | |
| CADI analysis (3-months) | 135 | 1.18 ± 1.76 [0-9] |
| CADI analysis (12-months) | 101 | 2.09 ± 2.49 [0-10] |
| eGFR analysis (6-months) | 139 | 57.40 ± 17.4 ml/min [15.08-116.37] |
| eGFR analysis (12-months) | 147 | 58.12 ± 19.45 ml/min [10.66-109.24] |

TABLE 3a

SNP distribution in genotyped Donors and Recipients in the GoCAR cohort (Donors = 468, Recipients = 540)

| | Whites | | Non-Whites | |
|---|---|---|---|---|
| Genotypes | Donor | Recipient | Donor | Recipient |
| A/A | 57 (16.1) | 59 (16.7) | 13 (11.4) | 10 (5.4) |
| A/G | 190 (53.7) | 187 (52.8) | 44 (38.6) | 65 (34.9) |
| G/G | 107 (30.2) | 108 (30.5) | 57 (50) | 109 (58.7) |
| A-allele (%) | 42.86 | 43.07 | 41.67 | 30.56 |
| Total | 354 | 354 | 114 | 186 |

TABLE 3b

Demographics & Race-wise distribution of non-white donors (114) and non-white recipients (186)

| | Afro-American | | Hispanic | | Asian | | Other* | |
|---|---|---|---|---|---|---|---|---|
| Genotypes | Donor | Recipient | Donor | Recipient | Donor | Recipient | Donor | Recipient |
| A/A | 1 (1.8) | 4 (3.6) | 9 (21.9) | 6 (19.4) | 1 (7.1) | 0 (0) | 2 (33.3) | 2 (11.1) |
| A/G | 23 (43.4) | 43 (39.1) | 17 (41.5) | 12 (38.7) | 3 (21.4) | 3 (11.1) | 1 (16.6) | 7 (38.9) |
| G/G | 29 (54.8) | 63 (57.3) | 15 (36.6) | 13 (41.9) | 10 (71.4) | 24 (88.9) | 3 (50) | 9 (50) |
| A-allele (%) | 23.58 | 23.18 | 42.68 | 38.70 | 17.85 | 11.11 | 41.67 | 30.56 |
| Total | 53 | 110 | 41 | 31 | 14 | 27 | 6 | 18 |

*Others - Patients of Pacific Islander, Native American, Unknown ethnicity

TABLE 4

QPCr primer sequences

| Gene name | Forward primer (5' → 3') | Reverse primer (5' → 3') |
|---|---|---|
| HGAPDH | TGTTGCCATCAATGACCCCTT (SEQ ID NO: 1) | CTCCACGACGTACTCAGCG (SEQ ID NO: 2) |
| Shroom3 | CCCTCTCGGGGCGTCTAGCC (SEQ ID NO: 3) | GCCCAGCACTACTCGCTCC (SEQ ID NO: 4) |
| Collagen-1 | GATGGTGAAGATGGTCCCAC (SEQ ID NO: 5) | GCCCAAGTCCAACTCCTTTT (SEQ ID NO: 6) |
| Fibronecctin-1 | TCCAGGAGTTCACTGTGCC (SEQ ID NO: 7) | CTGCAAGCCTTCAATAGTCA (SEQ ID NO: 8) |
| SNAIL | ACCACTATGCCGCGCTCTT (SEQ ID NO: 9) | GGTCGTAGGGCTGCTGGAA (SEQ ID NO: 10) |
| Matrix Metalloproteinase-2 | ACCCAGATGTGGCCAACTAC (SEQ ID NO: 11) | GAGCAAAAGGCATCATCCACT (SEQ ID NO: 12) |
| Vimentin | TTGACCTTGAACGCAAAGTG (SEQ ID NO: 13) | GCTGTTCCTGAATCTGAGCC (SEQ ID NO: 14) |
| E-Cadherin | CAGCACGTACACAGCCCTAA (SEQ ID NO: 15) | ACCTGAGGCTTTGGATTCCT (SEQ ID NO: 16) |
| Slug | GATGCATATTCGGACCCACAC (SEQ ID NO: 17) | CCTCATGTTTGTGCAGGAGAG (SEQ ID NO: 18) |
| FSP-1 | GCCCTGGATGTGATGGTGT (SEQ ID NO: 19) | TCGTTGTCCCTGTTGCTGTC (SEQ ID NO: 20) |
| SMA | CAACCGGGAGAAAATGACTC (SEQ ID NO: 21) | TAGATGGGGACATTGTGGGT (SEQ ID NO: 22) |

TABLE-5

Primer sequences designed for RT-PCR and generating Luciferase-Reporter plasmid constructs

| Primers | Forward primer (5' → 3') | Reverse primer (5' → 3') |
|---|---|---|
| HGAPDH | TGTTGCCATCAATGACCCCTT (SEQ ID NO:23) | CTCCACGACGTACTCAGCG (SEQ ID NO:24) |
| SHROOM3 | CCCTCTCGGGGCGTCTAGCC (SEQ ID NO:25) | GCCCAGCACTACTCGCTCCC (SEQ ID NO:26) |
| Constructs Wild-type (promoter only) | TTATAGGTACCTTGAGACAA-TAGAGTTGCC (SEQ ID NO:27) | TTAAGCTTCCATGCCAAA-CACATGATCCCTC (SEQ ID NO:28) |
| A-allele Construct | TTTGGTACCGAGTAGCAGGGC-AAAAACAAAAGCCCTTGAGAC-AATAGAGTTGCC (SEQ ID NO:29) | TTAAGCTTCCATGCCAAA-CACATGATCCCTC (SEQ ID NO: 30) |
| G-Allele Construct | TTTGGTACCGAGTAGCAGGG-CAAAAACAAAGGCCCTTGAG-ACAATAGAGTTGCC (SEQ ID NO:31) | TTAAGCTTCCATGCCAAA-CACATGATCCCTC (SEQ ID NO:32) |

Legend: KpnI was introduced in all forward primer and Hind III in the reverse ones.

REFERENCES

Coresh, J, Selvin, E, Stevens, L A, Manzi, J, Kusek, J W, Eggers, P, Van Lente, F and Levey, A S: Prevalence of chronic kidney disease in the United States. JAMA, 298: 2038-47, 2007.

Weiner, D E, Tighiouart, H, Amin, M G, Stark, P C, MacLeod, B, Griffith, J L, Salem, D N, Levey, A S & Sarnak, M J: Chronic kidney disease as a risk factor for cardiovascular disease and all-cause mortality: a pooled analysis of community-based studies. J Am Soc Nephrol, 15: 1307-15, 2004.

Chapman, J R, O'Connell, P J & Nankivell, B J: Chronic renal allograft dysfunction. J Am Soc Nephrol, 16: 3015-26, 2005.

Isoniemi H M, Krogerus L, von Willebrand E, Taskinen E, Ahonen J, Häyry P. Histopathological findings in well-functioning, long-term renal allografts. Kidney Int. 1992 January; 41(1):155-60.

Yilmaz S, McLaughlin K, Paavonen T, Taskinen E, Monroy M, Aavik E, Vamvakopoulos J, Häyry P. Clinical predictors of renal allograft histopathology: a comparative study of single-lesion histology versus a composite, quantitative scoring system. Transplantation. 2007 Mar. 27; 83(6): 671-6.

Magee J C, Barr M L, Basadonna G P, et al. Repeat Organ Transplantation in the United States, 1996-2005. American Journal of Transplantation 2007; 7 (Part 2): 1424-1433

USRDS 2012. http://www.usrds.org/2012/pdf/v2_ch7_12.pdf

Gago M, Cornell L D, Kremers W K, Stegall M D, Cosio F G. Kidney allograft inflammation and fibrosis, causes and consequences. Am J Transplant. 2012 May; 12(5):1199-207.

Rush D N, Henry S F, Jeffery J R, Schroeder T J, Gough J. Histological findings in early routine biopsies of stable renal allograft recipients. Transplantation 1994; 57: 208-211.

Seron D, Moreso F, Bover J, et al. Early protocol renal allograft biopsies and graft outcome. Kidney Int 1997; 51: 310-316.

Cosio F G, Grande J P, Larson T S, et al. Kidney allograft fibrosis and atrophy early after living donor transplantation. Am J Transplant 2005; 5: 1130-1136.

Park W D, Griffin M D, Cornell L D, Cosio F G, Stegall M D. Fibrosis with inflammation at one year predicts transplant functional decline. J Am Soc Nephrol 2010; 21: 1987-1997.

Akalin E, O'Connell P J. Genomics of chronic allograft injury. Kidney Int Suppl. 2010 December; (119):S33-7.

Akalin E, Hendrix R C, Polavarapu R G et al. Gene expression analysis in human renal allograft biopsy samples using high-density oligoarray technology. Transplantation 2001; 72: 948-953.

Flechner S M, Kurian S M, Head S R, Sharp S M, Whisenant T C, Zhang J, Chismar J D, Horvath S, Mondala T, Gilmartin T, Cook D J, Kay S A, Walker J R, Salomon D R. Kidney transplant rejection and tissue injury by gene profiling of biopsies and peripheral blood lymphocytes. Am J Transplant. 2004 September; 4(9):1475-89.

Donauer J, Rumberger B, Klein M, Faller D, Wilpert J, Sparna T, Schieren G, Rohrbach R, Dern P, Timmer J, Pisarski P, Kirste G, Walz G (2003) Expression profiling on chronically rejected transplant kidneys. Transplantation 76:539-547

Sarwal M, Chua M S, Kambham N, Hsieh S C, Satterwhite T, Masek M, Salvatierra O Jr. Molecular heterogeneity in acute renal allograft rejection identified by DNA microarray profiling. N Engl J Med. 2003 Jul. 10; 349(2):125-38.

Reeve J, Einecke G, Mengel M, Sis B, Kayser N, Kaplan B, Halloran P F. Diagnosing rejection in renal transplants: a comparison of molecular- and histopathology-based approaches. Am J Transplant. 2009 August; 9(8):1802-10. Epub 2009 Jun. 10

Scherer A, Krause A, Walker J R, Korn A, Niese D, Raulf F. Early prognosis of the development of renal chronic allograft rejection by gene expression profiling of human protocol biopsies. Transplantation. 2003 Apr. 27; 75(8): 1323-30.

Sagoo P, Perucha E, Sawitzki B, Tomiuk S, Stephens D A, Miqueu P, Chapman S, Craciun L, Sergeant R, Brouard S, Rovis F, Jimenez E, Ballow A, Giral M, Rebollo-Mesa I, Le Moine A, Braudeau C, Hilton R, Gerstmayer B, Bourcier K, Sharif A, Krajewska M, Lord G M, Roberts I, Goldman M, Wood K J, Newell K, Seyfert-Margolis V, Warrens A N, Janssen U, Volk H D, Soulillou J P, Hernandez-Fuentes M P, Lechler R I. Development of a cross-platform biomarker signature to detect renal transplant tolerance in humans. J Clin Invest. 2010 June; 120(6): 1848-61.

Newell K A, et al. Identification of a B cell signature associated with renal transplant tolerance in humans. J Clin Invest. 2010; 120(6):1836-1847.

Ju W, Eichinger F, Bitzer M, Oh J, McWeeney S, Berthier C C, Shedden K, Cohen C D, Henger A, Krick S, Kopp J B, Stoeckert C J Jr, Dikman S, Schröppel B, Thomas D B, Schlondorff D, Kretzler M, Böttinger E P. Renal gene and protein expression signatures for prediction of kidney disease progression. Am J Pathol. 2009 June; 174(6): 2073-85.

Kottgen, A, Glazer, N L, Dehghan, A, Hwang, S J, Katz, R, Li, M, Yang, Q, Gudnason, V, Launer, U, Harris, T B, Smith, A V, Arking, D E, Astor, B C, Boerwinkle, E, Ehret, G B, Ruczinski, I, Scharff, R B, Chen, Y D, de Boer, I H, Haritunians, T, Lumley, T, Sarnak, M, Siscovick, D, Benjamin, E J, Levy, D, Upadhyay, A, Aulchenko, Y S, Hofman, A, Rivadeneira, F, Uitterlinden, A G, van Duijn, C M, Chasman, D I, Pare, G, Ridker, P M, Kao, W H, Witteman, J C, Coresh, J, Shlipak, M G & Fox, C S: Multiple loci associated with indices of renal function and chronic kidney disease. Nat Genet, 41: 712-7, 2009

Boger, C A, Gorski, M, Li, M, Hoffmann, M M, Huang, C, Yang, Q, Teumer, A, Krane, V, O'Seaghdha, C M, Kutalik, Z, Wichmann, H E, Haak, T, Boes, E, Coassin, S, Coresh, J, Kollerits, B, Haun, M, Paulweber, B, Kottgen, A, Li, G, Shlipak, M G, Powe, N, Hwang, S J, Dehghan, A, Rivadeneira, F, Uitterlinden, A, Hofman, A, Beckmann, J S, Kramer, B K, Witteman, J, Bochud, M, Siscovick, D, Rettig, R, Kronenberg, F, Wanner, C, Thadhani, R I, Heid, I M, Fox, C S & Kao, W H: Association of eGFR-Related Loci Identified by GWAS with Incident CKD and ESRD. PLoS Genet, 7: e1002292. 2011

Hildebrand, J D & Soriano, P: Shroom, a PDZ domain-containing actin-binding protein, is required for neural tube morphogenesis in mice. Cell, 99: 485-97, 1999.

Hildebrand, J D: Shroom regulates epithelial cell shape via the apical positioning of an actomyosin network. J Cell Sci, 118: 5191-203, 2005.

Nishimura, T & Takeichi, M: Shroom3-mediated recruitment of Rho kinases to the apical cell junctions regulates epithelial and neuroepithelial planar remodeling. Development, 135: 1493-502, 2008.

Jin Y, Ratnam K, Chuang P Y, Fan Y, Zhong Y, Dai Y, Mazloom A R, Chen E Y, D'Agati V, Xiong H, Ross M J, Chen N, Ma'ayan A, He J C. A systems approach identifies HIPK2 as a key regulator of kidney fibrosis. Nat Med. 2012 Mar. 11; 18(4):580-8. doi: 10.1038/nm.2685

Gassmann, M., Grenacher, B., Rohde, B., and Vogel, J. (2009) Quantifying Western blots. Pitfalls of densitometry. Electrophoresis 30, 1845-1855

Henderson A R. Testing experimental data for univariate normality. Clin CChem Act. 2006 April; 366(1-2):112-29. Epub 2006 Jan. 4.

Paul L C. Chronic allograft nephropathy: an update. Kidney Int 1999; 56(3): 783.

Racusen L C, Regele H. The pathology of chronic allograft dysfunction. Kidney Int Suppl. 2010 December; (119): S27-32. Review.

Hariharan S, Johnson C P, Bresnahan B A, Taranto S E, McIntosh M J, Stablein D. Improved graft survival after renal transplantation in the United States, 1988 to 1996. N Engl J Med. 2000 Mar. 2; 342(9):605-12.

Nankivell B J, Borrows R J, Fung C L, O'Connell P J, Allen R D, Chapman J R. The natural history of chronic allograft nephropathy. N Engl J Med. 2003 Dec. 11; 349(24):2326-33.

Meier-Kriesche H U, Schold J D, Kaplan B. Long-term renal allograft survival: have we made significant progress or is it time to rethink our analytic and therapeutic strategies? Am J Transplant. 2004 August; 4(8):1289-95.

Lamb K E, Lodhi S, Meier-Kriesche H U. Long-term renal allograft survival in the United States: a critical reappraisal. Am J Transplant. 2011 March; 11(3):450-62. doi: 10.1111/j.1600-6143.2010.03283.x. Epub 2010 Oct. 25.

Solez K, Colvin R B, Racusen L C, Haas M, Sis B, Mengel M, Halloran P F, Baldwin W, Banfi G, Collins A B, Cosio F, David D S, Drachenberg C, Einecke G, Fogo A B, Gibson I W, Glotz D, Iskandar S S, Kraus E, Lerut E, Mannon R B, Mihatsch M, Nankivell B J, Nickeleit V, Papadimitriou J C, Randhawa P, Regele H, Renaudin K, Roberts I, Seron D, Smith R N, Valente M. Banff 07 classification of renal allograft pathology: updates and future directions. Am J Transplant. 2008 April; 8(4):753-60. Epub 2008 Feb. 19.

Halloran P F. Call for revolution: a new approach to describing allograft deterioration. Am J Transplant 2002; 2(3): 195.

Ying L, Sarwal M. In praise of arrays. Pediatr Nephrol (2009) 24:1643-1659.

Iglehart J K. Bundled payment for ESRD—including ESAs in Medicare's dialysis package. N Engl J Med. 2011 Feb. 17; 364(7):593-5.

Hotchkiss H, Chu T T, Hancock W W, Schroppel B, Kretzler M, Schmid H, Liu Y, Dikman S, Akalin E (2006) Differential expression of profibrotic and growth factors in chronic allograft nephropathy. Transplantation 81:342-349.

Ju W, Eichinger F, Bitzer M, Oh J, McWeeney S, Berthier C C, Shedden K, Cohen C D, Henger A, Krick S, Kopp J B, Stoeckert C J Jr, Dikman S, Schröppel B, Thomas D B, Schlondorff D, Kretzler M, Böttinger E P. Renal gene and protein expression signatures for prediction of kidney disease progression. Am J Pathol. 2009 June; 174(6):2073-85.

Mas V, Maluf D, Archer K, Yanek K, Mas L, King A, Gibney E, Massey D, Cotterell A, Fisher R, Posner M (2007) Establishing the molecular pathways involved in chronic allograft nephropathy for testing new noninvasive diagnostic markers. Transplantation 83:448-457.

Brennan E P, Morine M J, Walsh D W, Roxburgh S A, Lindenmeyer M T, Brazil D P, Gaora P Ó, Roche H M, Sadlier D M, Cohen C D; GENIE Consortium, Godson C, Martin F. Next-generation sequencing identifies TGF-β1-associated gene expression profiles in renal epithelial cells reiterated in human diabetic nephropathy. Biochim Biophys Acta. 2012 April; 1822 (4):589-99. Epub 2012 Jan. 14.

Ellis J W, Chen M H, Foster M C, Liu C T, Larson M G, de Boer I, Köttgen A, Parsa A, Bochud M, Böger C A, Kao L, Fox C S, O'Seaghdha C M; CKDGen Consortium; CARe Renal Consortium. Validated SNPs for eGFR and their associations with albuminuria. Hum Mol Genet. 2012 Jul. 15; 21(14):3293-8. doi: 10.1093/hmg/dds138. Epub 2012 Apr. 5.

Okada Y, Sim X, Go M J, et al. Meta-analysis identifies multiple loci associated with kidney function-related traits in east Asian populations. Nat Genet. 2012 Jul. 15; 44(8):904-9. doi: 10.1038/ng.2352.

Igo R P Jr, Iyengar S K, Nicholas S B, et al. Genomewide linkage scan for diabetic renal failure and albuminuria: the FIND study. Am J Nephrol. 2011; 33(5):381-9. Epub 2011 Mar. 31.

Xu T, Wu M, Feng J, Lin X, Gu Z. RhoA/Rho kinase signaling regulates transforming growth factor-β1-induced chondrogenesis and actin organization of synovium-derived mesenchymal stem cells through interaction with the Smad pathway. Int J Mol Med. 2012 November; 30(5):1119-25.

Satoh S, Yamaguchi T, Hitomi A, Sato N, Shiraiwa K, Ikegaki I, Asano T, Shimokawa H. Fasudil attenuates interstitial fibrosis in rat kidneys with unilateral ureteral obstruction. Eur J Pharmacol 2002; 455: 169-174

Nagatoya K, Moriyama T, Kawada N, Takeji M, Oseto S, Murozono T, Ando A, Imai E, Hori M. Y-27632 prevents tubulointerstitial fibrosis in mouse kidneys with unilateral ureteral obstruction. Kidney Int 2002; 61: 1684-1695

Takeda Y, Nishikimi T, Akimoto K, Matsuoka H, Ishimitsu T. Beneficial effects of a combination of Rho-kinase inhibitor and ACE inhibitor on tubulointerstitial fibrosis induced by unilateral ureteral obstruction. Hypertens Res. 2010 September; 33(9):965-73. Epub 2010 Jul. 22

ENCODE Project Consortium-Dunham I, et al. An integrated encyclopedia of DNA elements in the human genome. Nature. 2012 Sep. 6; 489(7414):57-74. doi: 10.1038/nature11247.

Neph S, Vierstra J, Stergachis A B, et al. An expansive human regulatory lexicon encoded in transcription factor footprints. Nature. 2012 Sep. 6; 489(7414):83-90. doi: 10.1038/nature11212.

Gerstein M B, Kundaje A, Hariharan M, et al. Architecture of the human regulatory network derived from ENCODE data. Nature. 2012 Sep. 6; 489(7414):91-100. doi: 10.1038/nature11245.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description. Patents, patent applications, publications, product descriptions, and protocols are cited throughout this application, the disclosures of which are incorporated herein by reference in their entireties for all purposes.

What is claimed is:

1. A method for treating a Caucasian allograft recipient that received a kidney allograft from a Caucasian kidney donor and is at an increased risk for developing Chronic Allograft Nephropathy (CAN) comprising the steps of
    (a) detecting the presence of an AA allele at the single nucleotide polymorphism (SNP) rs17319721 risk allele in a nucleic acid sample obtained from said Caucasian kidney donor using a nucleic acid-based detection assay, and
    (b) identifying said kidney allograft recipient as at an increased risk for developing CAN based on detection of said AA allele at the SNP rs17319721 risk allele detected in said nucleic acid sample obtained from said Caucasian kidney donor, and
    (c) administering an immunosuppressive drug to said kidney allograft recipient that received a kidney allograft from said Caucasian donor.

2. A method for treating- a Caucasian kidney allograft recipient who is at an increased risk of developing kidney fibrosis following receipt of a kidney allograft from a Caucasian kidney donor, comprising the steps of:
    (a) detecting expression of an AA allele at the single nucleotide polymorphism (SNP) rs 17319721 risk allele using a nucleic acid-based detection assay;
    (b) identifying said Caucasian kidney allograft recipient as at an increased risk of developing kidney fibrosis based on the detection of said AA allele at the SNP rs17319721 risk allele in the nucleic acid sample obtained from said Caucasian kidney donor, and
    administering an immunosuppressive drug to said kidney allograft recipient.

3. The method of claim 1 further comprising administering an angiotensin converting enzyme inhibitor to said kidney allograft recipient.

4. The method of claim 2 further comprising administering an angiotensin converting enzyme inhibitor to said kidney allograft-recipient.

5. The method of claim 1 wherein said nucleic acid sample comprises a blood sample obtained from said Caucasian kidney donor.

6. The method of claim 1 wherein said nucleic acid sample comprises a biopsy sample obtained from said kidney allograft.

7. The method of claim 2 wherein said nucleic acid sample comprises a blood sample obtained from said Caucasian kidney donor.

8. The method of claim 2 wherein said nucleic acid sample comprises a biopsy sample obtained from said kidney allograft.

9. A method for treating an intended kidney allograft recipient at risk of developing kidney fibrosis following the intended kidney allograft from a Caucasian kidney donor, comprising the steps of:
    detecting expression of an AA allele at the single nucleotide polymorphism (SNP) rs 17319721 risk allele in a nucleic acid sample obtained from the Caucasian kidney donor at baseline using a nucleic acid-based detection assay; and
    identifying said kidney allograft recipient as being at an increased risk of developing kidney fibrosis following the intended kidney allograft from a Caucasian kidney donor in the event that said AA allele at the SNP rs17319721 risk allele is detected in the nucleic acid sample obtained from said Caucasian kidney donor, and
    administering an immunosuppressive drug to said kidney allograft recipient that received a kidney allograft from said Caucasian donor.

* * * * *

SEQUENCE LISTING

```
<160> NUMBER OF SEQ ID NOS: 32

<210> SEQ ID NO 1
<211> LENGTH: 21
<212> TYPE: DNA
<213> ORGANISM: Artificial Sequence
<220> FEATURE:
<223> OTHER INFORMATION: synthetically generated oligonuelcotides

<400> SEQUENCE: 1
tgttgccatc aatgacccct t                                             21

<210> SEQ ID NO 2
<211> LENGTH: 19
<212> TYPE: DNA
<213> ORGANISM: Artificial Sequence
<220> FEATURE:
<223> OTHER INFORMATION: synthetically generated oligonuelcotides

<400> SEQUENCE: 2
ctccacgacg tactcagcg                                                19

<210> SEQ ID NO 3
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 3
ccctctcggg gcgtctagcc                                               20

<210> SEQ ID NO 4
<211> LENGTH: 19
<212> TYPE: DNA
<213> ORGANISM: Artificial Sequence
<220> FEATURE:
<223> OTHER INFORMATION: synthetically generated oligonuelcotides
```

```
<400> SEQUENCE: 4
gcccagcact actcgctcc                                                    19

<210> SEQ ID NO 5
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 5
gatggtgaag atggtcccac                                                   20

<210> SEQ ID NO 6
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 6
gcccaagtcc aactcctttt                                                   20

<210> SEQ ID NO 7
<211> LENGTH: 19
<212> TYPE: DNA
<213> ORGANISM: Artificial Sequence
<220> FEATURE:
<223> OTHER INFORMATION: synthetically generated oligonuelcotides

<400> SEQUENCE: 7
tccaggagtt cactgtgcc                                                    19

<210> SEQ ID NO 8
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 8
ctgcaagcct tcaatagtca                                                   20

<210> SEQ ID NO 9
<211> LENGTH: 19
<212> TYPE: DNA
<213> ORGANISM: Artificial Sequence
<220> FEATURE:
<223> OTHER INFORMATION: synthetically generated oligonuelcotides

<400> SEQUENCE: 9
accactatgc cgcgctctt                                                    19

<210> SEQ ID NO 10
<211> LENGTH: 19
<212> TYPE: DNA
<213> ORGANISM: Artificial Sequence
<220> FEATURE:
<223> OTHER INFORMATION: synthetically generated oligonuelcotides

<400> SEQUENCE: 10
ggtcgtaggg ctgctggaa                                                    19
```

```
<210> SEQ ID NO 11
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 11
acccagatgt ggccaactac                                              20

<210> SEQ ID NO 12
<211> LENGTH: 21
<212> TYPE: DNA
<213> ORGANISM: Artificial Sequence
<220> FEATURE:
<223> OTHER INFORMATION: synthetically generated oligonuelcotides

<400> SEQUENCE: 12
gagcaaaagg catcatccac t                                            21

<210> SEQ ID NO 13
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 13
ttgaccttga acgcaaagtg                                              20

<210> SEQ ID NO 14
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 14
gctgttcctg aatctgagcc                                              20

<210> SEQ ID NO 15
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 15
cagcacgtac acagccctaa                                              20

<210> SEQ ID NO 16
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 16
acctgaggct ttggattcct                                              20

<210> SEQ ID NO 17
<211> LENGTH: 21
<212> TYPE: DNA
<213> ORGANISM: Artificial Sequence
<220> FEATURE:
<223> OTHER INFORMATION: synthetically generated oligonuelcotides
```

```
<400> SEQUENCE: 17
gatgcatatt cggacccaca c                                              21

<210> SEQ ID NO 18
<211> LENGTH: 21
<212> TYPE: DNA
<213> ORGANISM: Artificial Sequence
<220> FEATURE:
<223> OTHER INFORMATION: synthetically generated oligonuelcotides

<400> SEQUENCE: 18
cctcatgttt gtgcaggaga g                                              21

<210> SEQ ID NO 19
<211> LENGTH: 19
<212> TYPE: DNA
<213> ORGANISM: Artificial Sequence
<220> FEATURE:
<223> OTHER INFORMATION: synthetically generated oligonuelcotides

<400> SEQUENCE: 19
gccctggatg tgatggtgt                                                 19

<210> SEQ ID NO 20
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 20
tcgttgtccc tgttgctgtc                                                20

<210> SEQ ID NO 21
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 21
caaccgggag aaaatgactc                                                20

<210> SEQ ID NO 22
<211> LENGTH: 20
<212> TYPE: DNA
<213> ORGANISM: Artificial Sequence
<220> FEATURE:
<223> OTHER INFORMATION: synthetically generated oligonuelcotides

<400> SEQUENCE: 22
tagatgggga cattgtgggt                                                20

<210> SEQ ID NO 23
<211> LENGTH: 21
<212> TYPE: DNA
<213> ORGANISM: Artificial Sequence
<220> FEATURE:
<223> OTHER INFORMATION: synthetic primer

<400> SEQUENCE: 23
tgttgccatc aatgacccct t                                              21
```

<210> SEQ ID NO 24
<211> LENGTH: 19
<212> TYPE: DNA
<213> ORGANISM: Artificial Sequence
<220> FEATURE:
<223> OTHER INFORMATION: synthetic primer

<400> SEQUENCE: 24
ctccacgacg tactcagcg                                                  19

<210> SEQ ID NO 25
<211> LENGTH: 20
<212> TYPE: DNA
<213> ORGANISM: Artificial Sequence
<220> FEATURE:
<223> OTHER INFORMATION: synthetic primer

<400> SEQUENCE: 25
ccctctcggg gcgtctagcc                                                 20

<210> SEQ ID NO 26
<211> LENGTH: 20
<212> TYPE: DNA
<213> ORGANISM: Artificial Sequence
<220> FEATURE:
<223> OTHER INFORMATION: synthetic primer

<400> SEQUENCE: 26
gcccagcact actcgctccc                                                 20

<210> SEQ ID NO 27
<211> LENGTH: 30
<212> TYPE: DNA
<213> ORGANISM: Artificial Sequence
<220> FEATURE:
<223> OTHER INFORMATION: synthetic primer

<400> SEQUENCE: 27
ttataggtac cttgagacaa tagagttgcc                                      30

<210> SEQ ID NO 28
<211> LENGTH: 31
<212> TYPE: DNA
<213> ORGANISM: Artificial Sequence
<220> FEATURE:
<223> OTHER INFORMATION: synthetic primer

<400> SEQUENCE: 28
ttaagcttcc atgccaaaca catgatccct c                                    31

<210> SEQ ID NO 29
<211> LENGTH: 54
<212> TYPE: DNA
<213> ORGANISM: Artificial Sequence
<220> FEATURE:
<223> OTHER INFORMATION: synthetic primer

<400> SEQUENCE: 29
tttggtaccg agtagcaggg caaaaacaaa agcccttgag acaatagagt tgcc            54

<210> SEQ ID NO 30
<211> LENGTH: 31
<212> TYPE: DNA
<213> ORGANISM: Artificial Sequence
<220> FEATURE:
<223> OTHER INFORMATION: synthetic primer

```
<400> SEQUENCE: 30
ttaagcttcc atgccaaaca catgatccct c                                31

<210> SEQ ID NO 31
<211> LENGTH: 54
<212> TYPE: DNA
<213> ORGANISM: Artificial Sequence
<220> FEATURE:
<223> OTHER INFORMATION: synthetic primer

<400> SEQUENCE: 31
tttggtaccg agtagcaggg caaaaacaaa ggcccttgag acaatagagt tgcc        54

<210> SEQ ID NO 32
<211> LENGTH: 31
<212> TYPE: DNA
<213> ORGANISM: Artificial Sequence
<220> FEATURE:
<223> OTHER INFORMATION: synthetic primer

<400> SEQUENCE: 32
ttaagcttcc atgccaaaca catgatccct c                                31
```